(12) United States Patent
Matsuura et al.

(10) Patent No.: US 9,569,842 B2
(45) Date of Patent: Feb. 14, 2017

(54) MEDICAL IMAGING APPARATUS

(71) Applicant: Toshiba Medical Systems Corporation, Otawara-shi (JP)

(72) Inventors: Masakazu Matsuura, Nasushiobara (JP); Katsuhito Morino, Utsunomiya (JP); Tomoyasu Komori, Otawara (JP); Yasunobu Yamada, Nasushiobara (JP); Hisashi Yasuda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 19 days.

(21) Appl. No.: 14/808,861

(22) Filed: Jul. 24, 2015

(65) Prior Publication Data

US 2015/0332456 A1 Nov. 19, 2015

Related U.S. Application Data

(63) Continuation of application No. PCT/JP2014/051502, filed on Jan. 24, 2014.

(30) Foreign Application Priority Data

Jan. 25, 2013 (JP) ................. 2013-012321
Jan. 24, 2014 (JP) ................. 2014-010923

(51) Int. Cl.
*G06K 9/00* (2006.01)
*G06T 7/00* (2006.01)
(Continued)

(52) U.S. Cl.
CPC ............ *G06T 7/0012* (2013.01); *A61B 6/037* (2013.01); *A61B 6/469* (2013.01); *A61B 6/5205* (2013.01);
(Continued)

(58) Field of Classification Search
CPC ................ A61B 6/00; G06T 7/00; G06K 9/00
(Continued)

(56) References Cited

U.S. PATENT DOCUMENTS 7,672,421 B2 * 3/2010 Chen ..................... G06T 11/005
378/4
2011/0297834 A1 12/2011 Komori et al.
2013/0028500 A1 1/2013 Takahashi et al.

FOREIGN PATENT DOCUMENTS

JP 2006-025868 A 2/2006
JP 2010-203807 A 9/2010
(Continued)

OTHER PUBLICATIONS

International Search Report mailed May 13, 2014 for PCT/JP2014/051502 filed Jan. 24, 2014 with English Translation.

*Primary Examiner* — Abolfazl Tabatabai
(74) *Attorney, Agent, or Firm* — Oblon, McClelland, Maier & Neustadt, L.L.P.

(57) ABSTRACT

A medical imaging apparatus includes a reconstruction unit, a ROI setting unit, and a controller. The reconstruction unit receives projection data that is based on radiation detected by a detector, divides the projection data into a plurality of subsets, and apply a reconstruction process to the subsets by successive approximation to successively generate images. The ROI setting unit sets a ROI in the images. The controller obtains a variation value indicating a change in image quality from the images, and, when the variation value reaches a predetermined value, instructs the reconstruction unit on a new subset count less than the number of the subsets to sequentially reconstruct subsets as many as the new subset count into an image. The reconstruction unit assigns a weight to the projection data based on the ROI, and divides the projection data into the subsets based on the weight.

8 Claims, 17 Drawing Sheets

(51) Int. Cl.
*G06T 11/00* (2006.01)
*A61B 6/00* (2006.01)
*A61B 6/03* (2006.01)
*A61B 5/05* (2006.01)

(52) U.S. Cl.
CPC ........... G06T 7/0081 (2013.01); G06T 11/003 (2013.01); *G06T 2207/10004* (2013.01); *G06T 2207/10081* (2013.01); *G06T 2207/10104* (2013.01); *G06T 2207/10116* (2013.01); *G06T 2207/20104* (2013.01); *G06T 2207/30004* (2013.01); *G06T 2210/41* (2013.01)

(58) Field of Classification Search
USPC ....... 382/128, 129, 130, 131, 132, 133, 134; 600/407, 425, 427
See application file for complete search history.

(56) References Cited

FOREIGN PATENT DOCUMENTS

JP      2012-011181 A      1/2012
WO    WO 2011/122613 A1   10/2011

\* cited by examiner

PROGRESS OF RECONSTRUCTION PROCESS

MEDICAL IMAGING APPARATUS

CROSS-REFERENCE TO RELATED APPLICATION

This application is based upon and claims the benefit of priority from Japanese Patent Application Nos. 2013-012321, filed Jan. 25, 2013 and 2014-010923, filed Jan 24, 2014; the entire contents of which are incorporated herein by reference.

FIELD

Embodiments described herein relate generally to a medical imaging apparatus.

BACKGROUND

Positron emission tomography (PET) devices and single photon emission computed tomography (SPECT) devices are used to capture an image representing the internal function of a subject. In the photographing by a PET device, a drug labeled with various positron emissions is administered to the subject. The PET device detects the radiation caused by that positrons emitted from the various positron emissions combine with negatrons and disappear. In the photographing by an SPECT device, a drug labeled with a radioactive isotope is administered to the subject. The SPECT device detects the radiation emitted from the radioactive isotope. Besides, X-ray computed tomography (CT) devices are used to capture an image representing the internal structure of a subject. An X-ray CT device irradiates the subject with X-rays from different directions a plurality of times, and detects X-rays having passed through the subject with an X-ray detector.

These devices generate an image representing the internal structure of the subject based on projection data obtained by the detection. At this time, some devices apply a reconstruction process to the projection data by a block iterative successive approximation method to generate the image. In the block iterative successive approximation method, the projection data is divided into a plurality of subsets, and successive approximation is performed on each of the subsets. When such division of the projection data into subsets (subsetting) is performed, the time required for the successive approximation (the time required for the reconstruction process) is reduced compared to the case without the subsetting.

Meanwhile, the subsetting causes degradation of the image quality. This is due to a bias in statistical errors contained in each subset. In other words, the block iterative successive approximation is known as a method in which an increase in the number of subsets reduces the time required for the reconstruction process and also degrades the image quality. Accordingly, the generation of an image with good image quality requires less number of subsets and long-time reconstruction process. If the number of subsets is increased to reduce the time taken for the reconstruction process, the image quality is lowered.

DETAILED DESCRIPTION

Figure 1:
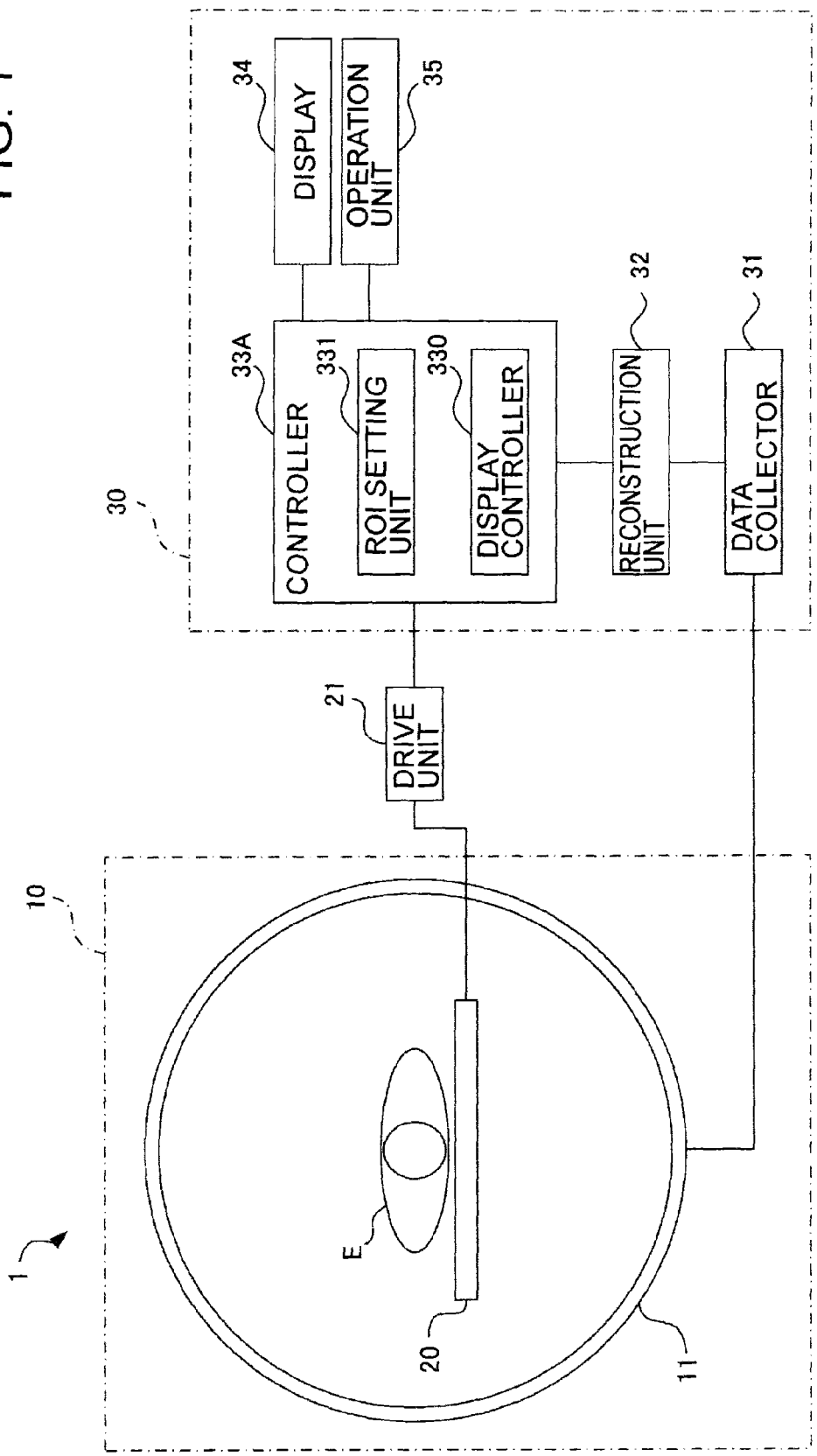
FIG. 1 is a block diagram illustrating the configuration of a medical imaging apparatus according to an embodiment.

In general, according to one embodiment, a medical imaging apparatus includes a detector, a reconstruction unit, a ROI setting unit, and a controller. The detector detects radiation. The reconstruction unit receives projection data that is based on the radiation detected by the detector, divides the projection data into a plurality of subsets, and apply a reconstruction process to the subsets by successive approximation to successively generate images. The ROI setting unit sets a ROI in the images. The controller obtains a variation value indicating a change in image quality from the images, and, when the variation value reaches a predetermined value, instructs the reconstruction unit on a new subset count less than the number of the subsets to sequentially reconstruct subsets as many as the new subset count into an image. The reconstruction unit assigns a weight to the projection data based on the ROI, and divides the projection data into the subsets based on the weight.

Referring now to the drawings, a description is given of the medical imaging apparatus according to embodiments. In the following, "image" and "image data" are in one-to-one correspondence with each other, and therefore, may be equated with each other.

First Embodiment

Configuration

With reference to FIG. 1, a description is given of an example of the configuration of a PET device as a medical imaging apparatus 1 according to an embodiment.

The medical imaging apparatus 1 includes a gantry, a couch 20, and a console 30.

The gantry detects the radiation emitted from a subject E. The gantry has an opening that allows insertion of the subject E placed on the couch 20. The gantry includes detectors 11. The detectors 11 detect radiation. The detectors 11 are arranged in a number of rings along the opening to surround it. The rings are arranged in multiple layers along the axis of the opening. The detectors 11 detect radiation in the range of the array width along the axis of the opening.

The gantry and the couch 20 move relative to each other. The couch 20 includes a drive unit 21. In response to an instruction from a controller 33A, the drive unit 21 moves the couch 20 in the body axis direction of the subject E. Thereby, the gantry and the couch 20 move relatively. By the relative movement of the gantry and the couch 20, that is, the relative movement of the gantry and the subject E, the detectors 11 are positioned around a radiation emission point in the subject E. The radiation emitted from the radiation emission point in the range of the array width of the detectors 11 is incident on the detectors 11. The detectors 11 detect the incident radiation.

The console 30 includes a data collector 31, a reconstruction unit 32, the controller 33A, a display 34, and an operation unit 35. The data collector 31 counts the quantum of the radiation detected by the detectors 11 to collect projection data.

The reconstruction unit 32 receives the projection data that is based on the radiation detected by the detectors 11 from the data collector 31. The reconstruction unit 32 divides the projection data into a plurality of subsets, and also applies a reconstruction process to the subsets by successive approximation to successively generate images. For example, when dividing the projection data into a plurality of subsets, the reconstruction unit 32 assigns a subset number m (m: a natural number from 1 to M) to each subset. The reconstruction unit 32 performs the reconstruction process by using an analysis model formed of three-dimensional arrays of a plurality of voxels. The reconstruction unit 32 performs the reconstruction process by successive approximation for each subset to estimate the density value of a positron-emitting nuclide in a position in the subject E corresponding to each voxel. The reconstruction unit 32 calculates an estimated value of the k-th update (k: a natural number) in the update count, and performs k+1-th calculation using the k-th estimated value calculated. Here, the update count represents the number of times the reconstruction unit 32 performs an approximation process (the calculation of the estimated value) with respect to subsets. For example, when the number of subsets is "10", if the approximation process is performed on each of the 10 subsets, the update count is "10". The estimated value calculated in this way corresponds to the value of the voxel. The calculation of the estimated value by the reconstruction unit 32 corresponds to the update of the voxel value.

The reconstruction unit 32 performs the approximation process for the m-th subset to calculate an estimated density of the position in the subject E corresponding to each voxel. The reconstruction unit 32 determines whether the subset number m is the maximum value M. If the subset number m is not the maximum value M, the reconstruction unit 32 increments the subset number m and the update count k, and performs the approximation process to calculate an estimated density related to a new subset. When the subset number m is the maximum value M, the reconstruction unit 32 determines whether the estimated density calculated has converged. When the estimated density has converged, the reconstruction unit 32 ends the reconstruction process. When the estimated density has not converged, the reconstruction unit 32 determines whether an iteration count n is the upper limit value L. Here, the iteration count represents the number of times a round of the approximation process for each subset (the calculation of an estimated value) is performed. For example, when the number of subsets is "10", the reconstruction unit 32 performs the approximation process for each of the subsets with a subset number from "1" to "10", and further performs the approximation process for each of them. The number of repetitions is the iteration count. If the iteration count n is not the upper limit value L, the reconstruction unit 32 sets the subset number m at "1" as well as incrementing the iteration count to calculate the estimated density for a subset with the subset number "1". When the iteration count n is the upper limit value L, the reconstruction unit 32 ends the reconstruction process.

In response to an instruction to reduce the number of subsets from the controller 33A, the reconstruction unit 32 divides the projection data into the reduced number of subsets. The reconstruction unit 32 performs the reconstruction process described above with respect to the new number of subsets obtained by the division.

The controller 33A obtains, from images successively generated, a variation value indicating a variation in the quality of the images. When the variation value reaches a predetermined value, the controller 33A instructs the reconstruction unit 32 on a new subset count indicating the reduced number of subsets to sequentially reconstruct subsets as many as the new subset count into an image.

The controller 33A includes an ROI setting unit 331. The ROI setting unit 331 sets a region of interest (ROI) in the image obtained by the reconstruction unit 32. The ROI setting unit 331 sets image regions corresponding to different tissues in the subject E as ROIs. In response to an instruction from the operation unit 35, the ROI setting unit 331 sets the ROIs.

The controller 33A sequentially receives image data generated by the reconstruction process from the reconstruction unit 32, and obtains a difference or a ratio of average values of pixel values contained in determined ROIs as a variation value, thereby controlling the reconstruction unit 32 to reduce the number of subsets based on the difference or the ratio. At this time, the controller 33A calculates an average value of pixels included in each ROI to obtain a difference or a ratio of average values thus calculated. Here, the difference or the ratio of average values of pixel values included in ROIs corresponds to the contrast of the image. Usually, in the course of the reconstruction process, the difference and the ratio (contrast) are known to be increased. Therefore, the controller 33A can determine the progress of the reconstruction process by monitoring the difference or the ratio of average values of pixels included in ROIs as a variation value. The controller 33A receives image data from the reconstruction unit 32 each time the reconstruction unit 32 updates the image. Alternatively, the controller 33A may receive image data from the reconstruction unit 32 each time the image is updated a predetermined number of times.

The controller 33A includes, for example, a processing unit and a storage device. Examples of the processing unit include, for example, a central processing unit (CPU), a graphics processing unit (GPU), and an application specific integrated circuit (ASIC). Examples of the storage device include a read only memory (ROM), a random access memory (RAM), and a hard disc drive (HDD). The storage device stores computer programs for implementing the functions of the units of the medical imaging apparatus 1.

The processing unit executes the computer programs to implement the above functions. The controller 33A controls each unit of the apparatus.

The storage device of the controller 33A stores in advance a first reference value for determining the progress of the reconstruction process. For example, the storage device stores, in stages, a plurality of differences or ratios of average values of pixels included in ROIs each as a variation value in association with the first reference value. The controller 33A compares the difference or the ratio obtained to the first reference value. When the difference or the ratio is equal to or larger than the first reference value, the controller 33A issues an instruction to reduce the number of subsets to the reconstruction unit 32. With respect to an image obtained by performing the approximation process on new subsets, the controller 33A makes the determination with a new first reference value. Besides, when issuing the instruction to reduce the number of subsets to the reconstruction unit 32, the controller 33A also outputs the reduced number of subsets.

Figure 2:
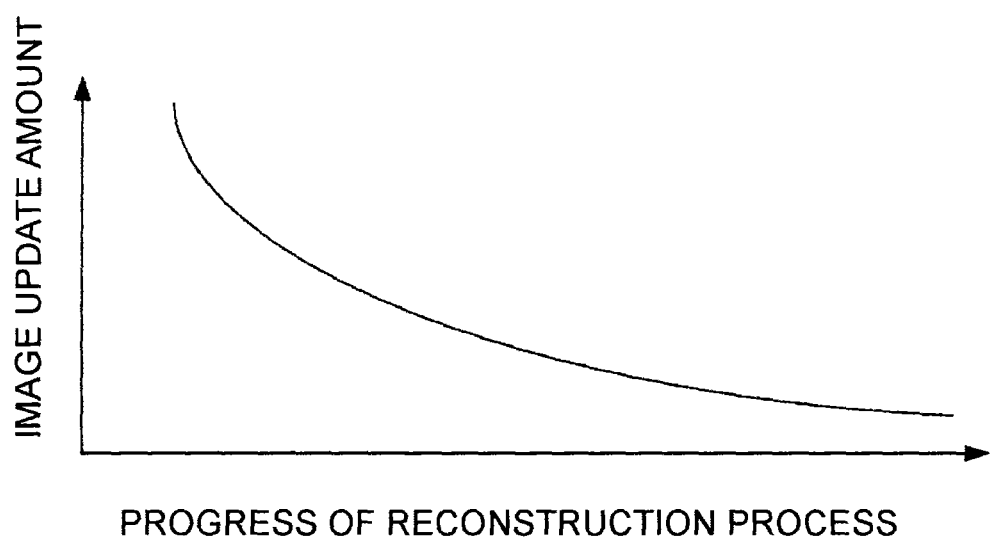
FIG. 2 is a schematic diagram illustrating the outline of the medical imaging apparatus of the embodiment.

Described below is a background where degradation in the image quality caused by the division into subsets to shorten the time taken for the reconstruction process is improved. FIG. 2 is a diagram qualitatively illustrating a relationship between the progress of the reconstruction process and an image update amount in the reconstruction process. The image update amount is the difference between the k-th estimated value and the k+1-th estimated value. A reconstructed image is obtained in each subset, thereby the update count of the image is increased, and thus a reconstructed image with preferable image quality for diagnosis can be obtained faster. This leads to less reconstruction process time. However, since projection data is divided into subsets, the balance of noise in each subset is destroyed, and also each subset is brought to have a maximum-likelihood estimation solution of successive approximation reconstruction. As a result, the image quality degradation occurs. In the embodiment, the division number of subsets is changed during the reconstruction process, which improves the noise balance of a reconstructed image and achieves a unique maximum-likelihood estimation solution. This results in solving the adverse effects caused by the division into subsets described above, and thus the image quality degradation is reduced. Therefore, less reconstruction process time as well as improved image quality can be achieved.

A display controller 330 receives the image data from the reconstruction unit 32, generates an image that represents the internal structure of the subject E, and displays the image on the display 34. For example, the display controller 330 is capable of multiplanar reformation (MPR) and volume rendering. The MPR is image processing in which rendering is performed by setting an arbitrary cross section in the image data generated by the reconstruction unit to generate MPR image data representing the cross section. The volume rendering is image processing in which volume data is sampled along an arbitrary line of sight (ray), and the values (estimated density values) are added up to generate pseudo three-dimensional image data that represents a three-dimensional region of the subject E.

The storage stores detection data, projection data, image data after the reconstruction process, and the like. The display 34 is formed of a liquid crystal display (LCD) device. The operation unit 35 is used to enter various instructions and information to the medical imaging apparatus 1. The operation unit 35 includes, for example, a keyboard, a mouse, a track ball, and the like. The operation unit 35 may also include a graphical user interface (GUI) displayed on the display 34.

[Operation]

Figure 3:
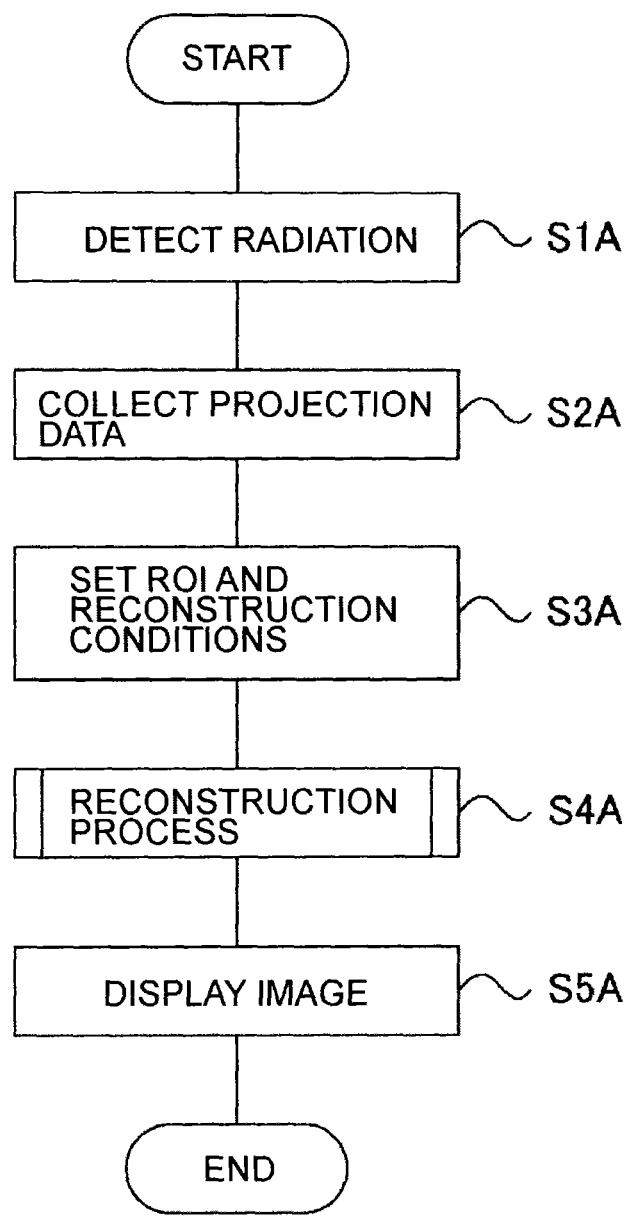
FIG. 3 is a flowchart of the operation of the medical imaging apparatus of the embodiment.
Figure 4:
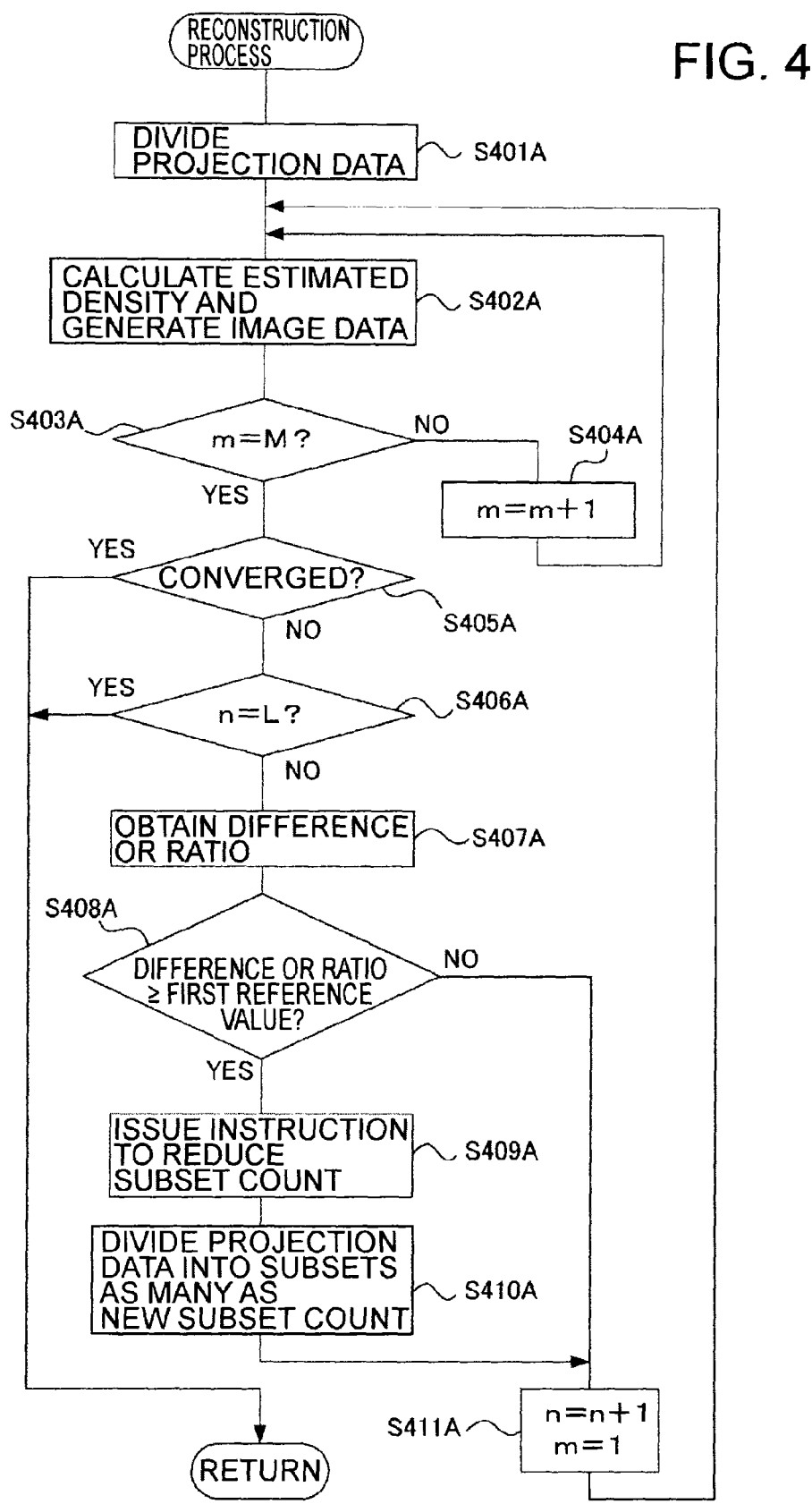
FIG. 4 is a flowchart of the operation of the medical imaging apparatus of the embodiment.

FIGS. 3 and 4 are flowcharts illustrating the operation of the medical imaging apparatus 1 of this embodiment.

(S1A)

The subject E is placed on the couch 20, and is inserted into the opening of the detectors 11. The controller 33A controls the detectors 11 to detect radiation from the subject E. The detectors 11 output the detection result to the data collector 31.

(S2A)

Under the control of the controller 33A, the data collector 31 receives the detection result of the detectors 11, and collects projection data by quantum counting the radiation according to the detection result. The data collector 31 outputs the projection data to the reconstruction unit 32.

(S3A)

The controller 33A controls the ROI setting unit 331 to set ROIs. In addition, the controller 33A sets a subset count and the upper limit value L of the iteration count n as reconstruction conditions. The reconstruction conditions may include various items (may be referred to as "condition items") as other conditions. Examples of the condition items include a field of view (FOV). The FOV is a condition item which defines the field size. The FOV is set with reference to an image based on the projection data. Alternatively, a predetermined FOV may be set automatically.

(S4A)

Under the control of the controller 33A, the reconstruction unit 32 receives the projection data generated based on the radiation detected by the detectors 11 from the data collector 31. The reconstruction unit 32 divides the projection data into a plurality of subsets based on the reconstruction conditions set in step S3A, and also applies the reconstruction process to the subsets by successive approximation to successively generate images. FIG. 4 is a flowchart illustrating the operation for the reconstruction process.

(S401A)

The reconstruction unit 32 divides the projection data received from the data collector 31 into a plurality of subsets. At this time, the number of the subsets is as many as the subset count set in step S3A. In other words, the subset number m can take a value from 1 to the maximum value M.

(S402A)

The reconstruction unit 32 first performs the approximation process for the first subset (m=1) to calculate an estimated density of the position in the subject E corresponding to each voxel, and generates image data based on the estimated density calculated.

(S403A)

The reconstruction unit 32 determines whether the subset number m of the subset, for which the estimated density is calculated in step S402A, is the maximum value M. When the subset number m is not the maximum value M, the process proceeds to step S404A. When the subset number m is the maximum value M, it proceeds to step S405A.

(S404A)

The controller 33A controls the reconstruction unit 32 to increment the subset number m. Then, returning back to step S402A, the process is performed on a subset assigned with the subset number m incremented.

(S405A)

The controller 33A determines whether the estimated density calculated has converged. The controller 33A may make this determination by a general method such as using a log likelihood function. When the controller 33A has determined that the estimated density has converged, the process proceeds to step S5A in FIG. 3. When the controller 33A has determined that it has not converged, the process proceeds to step S406A.

(S406A)

The controller 33A determines whether the iteration count n is the upper limit value L. When the iteration count n is the upper limit value L, the process proceeds to step S5A in FIG. 3. When the iteration count n is not the upper limit value L, the process proceeds to step S407A.

(S407A)

The controller 33A receives the image data generated by the reconstruction unit 32 in step S402A, and obtains a difference or a ratio of average values of pixels included in the ROIs as a variation value. At this time, the controller 33A calculates an average value of pixels included in each ROI to calculate the difference or the ratio of the average values.

(S408A)

The controller 33A compares the difference or the ratio thus obtained to the first reference value stored in advance. When the difference or the ratio is not equal to or larger than the first reference value, the process proceeds to step S411A. When the difference or the ratio is equal to or larger than the first reference value, the process proceeds to step S409A.

(S409A)

The controller 33A issues an instruction to reduce the number of subsets and the reduced number of subsets to the reconstruction unit 32, and changes the maximum value M to a new subset count after the reduction. Further, the controller 33A retrieves the first reference value associated with the new subset count from the storage device.

(S410A)

The controller 33A controls the reconstruction unit 32 to divide the projection data into subsets as many as the new subset count.

(S411A)

The controller 33A controls the reconstruction unit 32 to increment the iteration count n. The controller 33A further controls the reconstruction unit 32 to change the subset number m to "1".

(S5A)

Under the control of the controller 33A, the display controller 330 receives the image data from the reconstruction unit 32. The display controller 330 generates an image representing the internal structure of the subject E, and displays the image on the display 34. Thus, the operation illustrated in FIG. 3 is completed.

According to this embodiment, the medical imaging apparatus 1 includes the detectors 11, the reconstruction unit 32, and the controller 33A. The detectors 11 are configured to detect radiation. The reconstruction unit 32 is configured to receive projection data that is based on the radiation detected by the detectors 11, divide the projection data into a plurality of subsets, and apply a reconstruction process to the subsets by successive approximation to successively generate images. The controller 33A is configured to monitor a course of the reconstruction process performed by the reconstruction unit 32, and control the reconstruction unit 32 to reduce a subset count indicating the number of subsets based on a variation value obtained by monitoring. The controller 33A includes the ROI setting unit 331 configured to set a ROI in the images. The controller 33A is configured to calculate a difference or a ratio of average values of pixels included in ROIs set in the images as the variation value, and control the reconstruction unit 32 to reduce the subset count based on the difference or the ratio. In this manner, the medical imaging apparatus 1 obtains a difference or a ratio of average values of pixels included in ROIs as a variation value for the reconstruction process, and reduces the number of subsets based on the variation value. That is, the medical imaging apparatus 1 operates such that the subset count is larger in the early stage of the reconstruction process, while the subset count is reduced in the late stage. Thus, the medical imaging apparatus 1 can achieve less reconstruction process time as well as improved image quality.

Second Embodiment

Configuration

Figure 5:
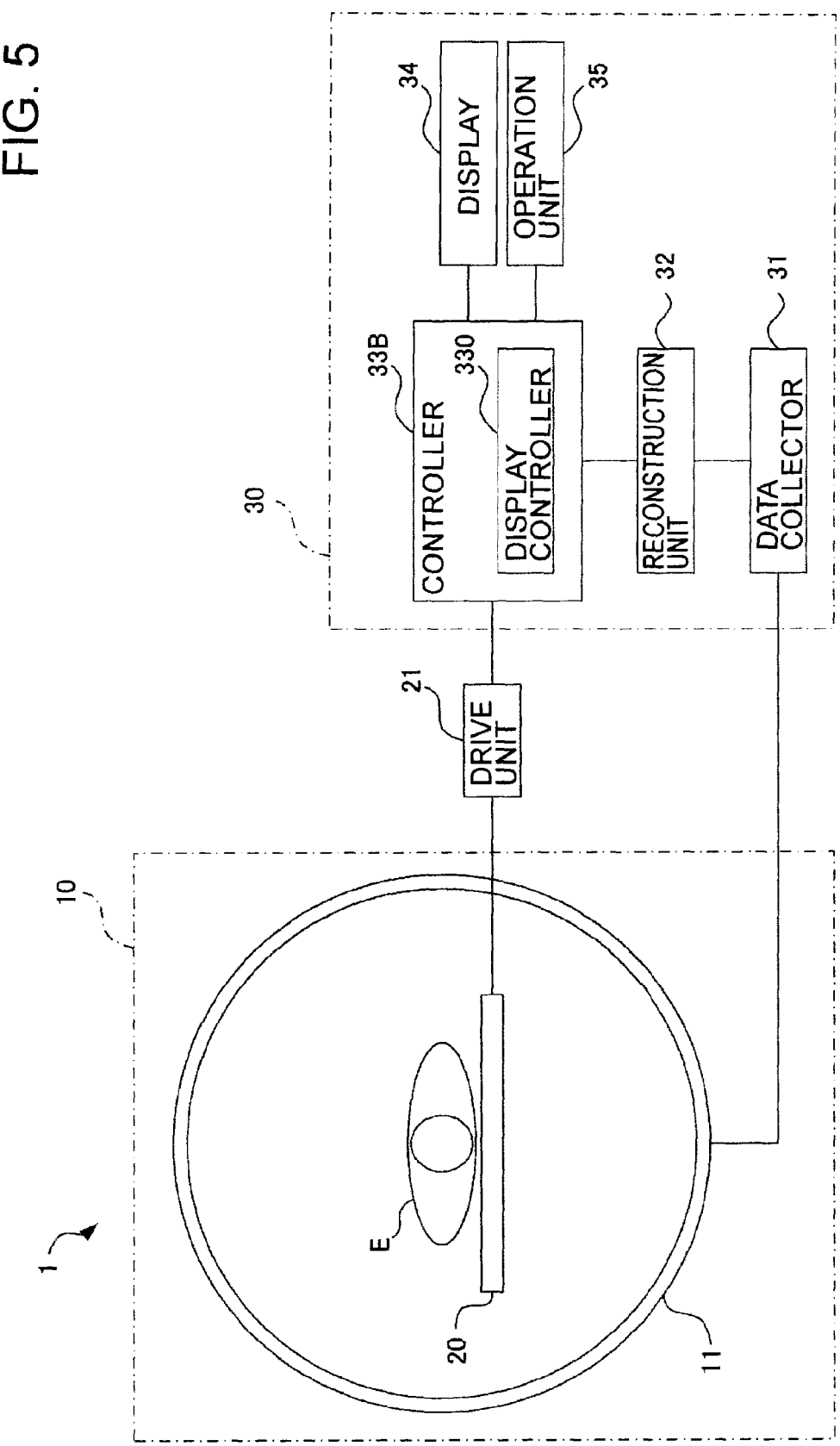
FIG. 5 is a block diagram illustrating the configuration of a medical imaging apparatus according to an embodiment.

FIG. 5 is a block diagram of the medical imaging apparatus 1 according to a second embodiment. The second embodiment is different from the first embodiment in the configuration of a controller 33B. Otherwise, this embodiment is similar to the first embodiment.

The controller 33B sequentially acquires images from the reconstruction unit 32, and obtains a variance or standard deviation of the pixel values of the images as a variation value. The controller 33B controls the reconstruction unit 32 to reduce the number of subsets based on the variance or the standard deviation. At this time, the controller 33B calculates a variance or standard deviation of pixels included in the images acquired. In general, projection data contains noise, which also appears as noise in the image quality of the reconstructed image. The high-frequency components of the noise are reconstructed as an image in the late stage of the reconstruction process by a successive approximation reconstruction method. Thus, in the course of the reconstruction process, the variance or the standard deviation increases. Accordingly, the controller 33B monitors the variance or standard deviation of images as a variation value to determine the progress of the reconstruction process. The controller 33B receives image data from the reconstruction unit 32 each time the reconstruction unit 32 updates an image. The controller 33B may receive image data from the reconstruction unit 32 each time image update is performed a predetermined number of times. The effect of noise on the image quality is smaller as the number of subsets reduces. Therefore, the controller 33B can improve the image quality by reducing the number of subsets.

The controller 33B includes, for example, a processing unit and a storage device. The storage device of the controller 33B stores in advance a second reference value for determining the progress of the reconstruction process. For example, the storage device stores, in stages, a plurality of variances or standard deviations of pixels included in images each as a variation value in association with the second reference value. The controller 33B compares the variance or the standard deviation to the second reference value. When the variance or the standard deviation is equal to or larger than the second reference value, the controller 33B issues an instruction to reduce the number of subsets to the reconstruction unit 32. Besides, when issuing the instruction to reduce the number of subsets to the reconstruction unit 32, the controller 33B also outputs the reduced number of subsets.

[Operation]

Figure 6:
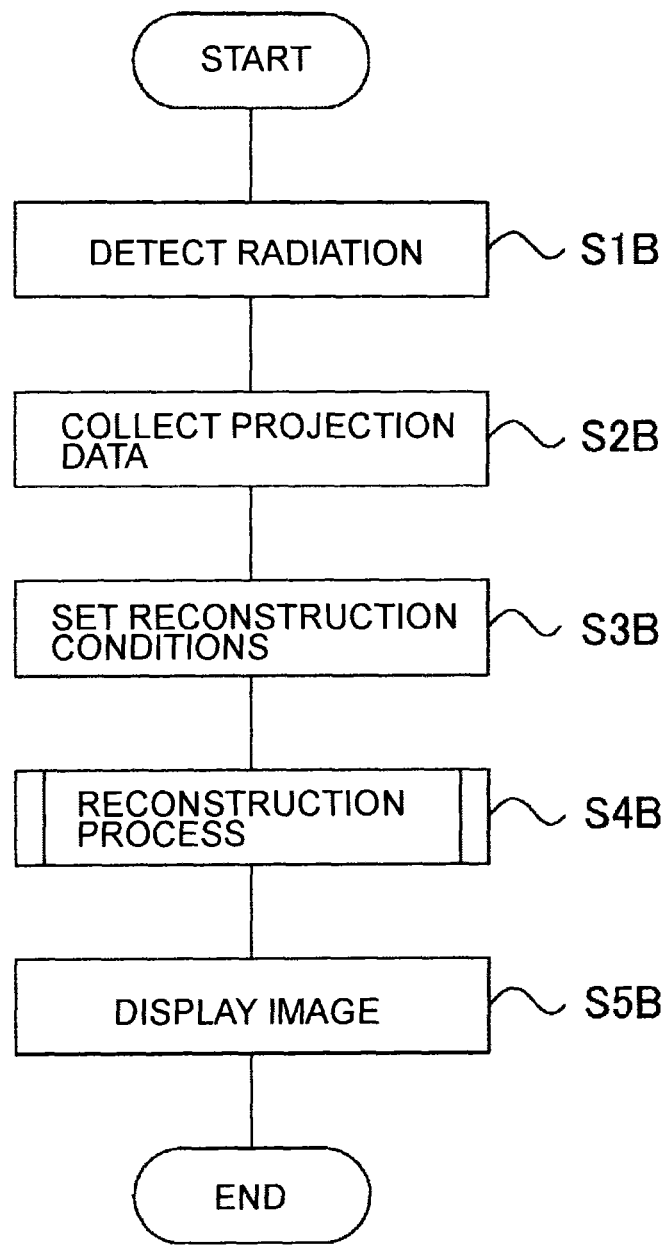
FIG. 6 is a flowchart of the operation of the medical imaging apparatus of the embodiment.
Figure 7:
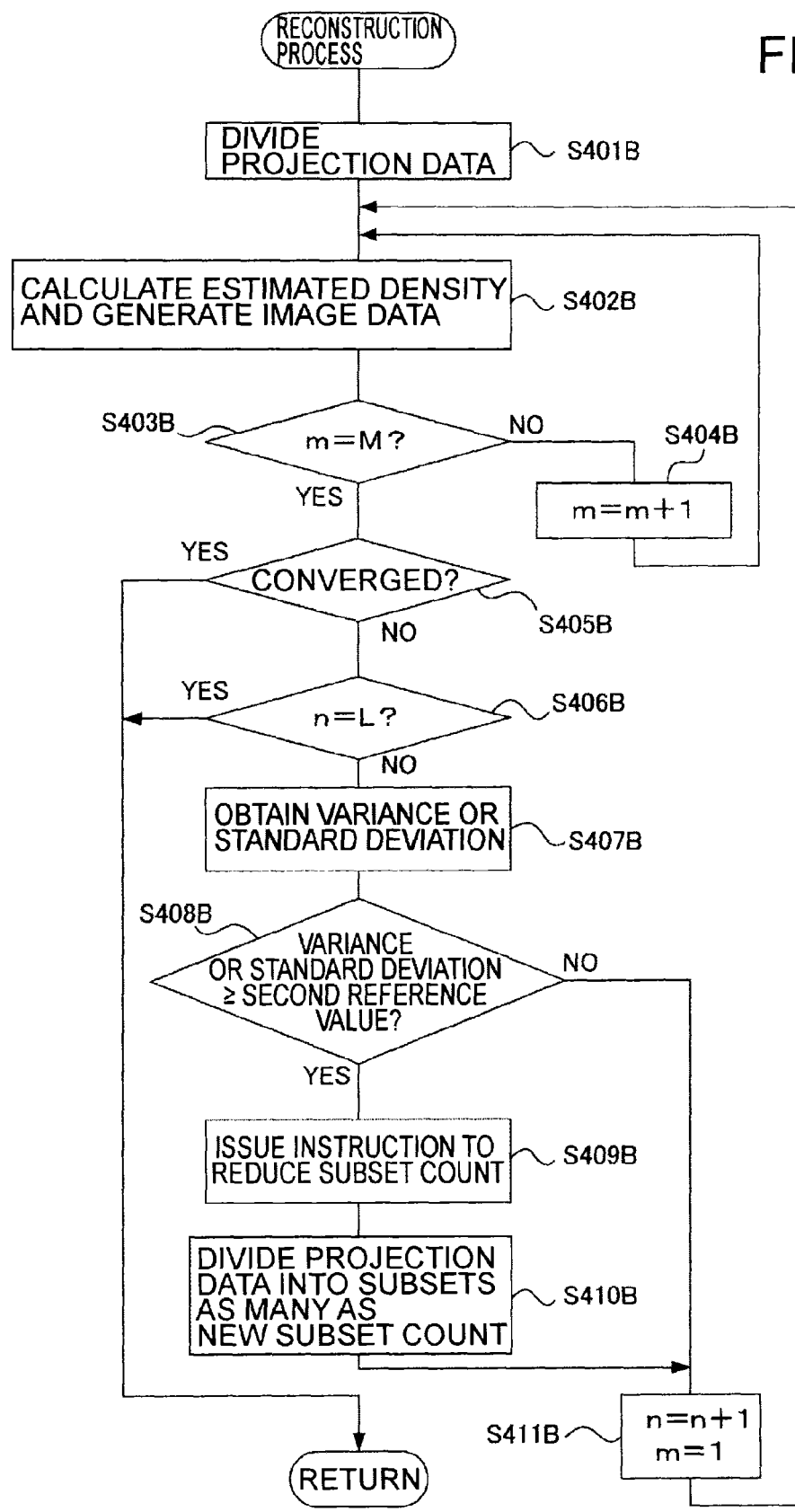
FIG. 7 is a flowchart of the operation of the medical imaging apparatus of the embodiment.

FIGS. 6 and 7 are flowcharts illustrating the operation of the medical imaging apparatus 1 of this embodiment.

(S1B)

The subject E is placed on the couch 20, and is inserted into the opening of the detectors 11. The controller 33B controls the detectors 11 to detect radiation from the subject E. The detectors 11 output the detection result to the data collector 31.

(S2B)

Under the control of the controller 33B, the data collector 31 receives the detection result of the detectors 11, and collects projection data by quantum counting the radiation according to the detection result. The data collector 31 outputs the projection data to the reconstruction unit 32.

(S3B)

The controller 33B sets a subset count and the upper limit value L of the iteration count n as reconstruction conditions. The reconstruction conditions may include various items (may be referred to as "condition items") as other conditions. Examples of the condition items include a field of view (FOV). The FOV is a condition item which defines the field size. The FOV is set with reference to an image based on the projection data. Alternatively, a predetermined FOV may be set automatically.

(S4B)

Under the control of the controller 33B, the reconstruction unit 32 receives the projection data generated based on the radiation detected by the detectors 11 from the data collector 31. The reconstruction unit 32 divides the projection data into a plurality of subsets based on the reconstruction conditions set in step S3B, and also applies the reconstruction process to the subsets by successive approximation to successively generate images. FIG. 7 is a flowchart illustrating the operation for the reconstruction process.

(S401B)

The reconstruction unit 32 divides the projection data received from the data collector 31 into a plurality of subsets. At this time, the number of the subsets is as many as the subset count set in step S3B. In other words, the subset number m can take a value from 1 to the maximum value M.

(S402B)

The reconstruction unit 32 first performs the approximation process for the first subset (m=1) to calculate an estimated density of the position in the subject E corresponding to each voxel, and generates image data based on the estimated density calculated.

(S403B)

The reconstruction unit 32 determines whether the subset number m of the subset, for which the estimated density is calculated in step S402B, is the maximum value M. When the subset number m is not the maximum value M, the process proceeds to step S404B. When the subset number m is the maximum value M, it proceeds to step S405B.

(S404B)

The controller 33B controls the reconstruction unit 32 to increment the subset number m. Then, returning back to step S402B, the process is performed on a subset assigned with the subset number m incremented.

(S405B)

The controller 33B determines whether the estimated density calculated has converged. The controller 33B may make this determination by a general method such as using a log likelihood function. When the controller 33B has determined that the estimated density has converged, the process proceeds to step S5B in FIG. 6. When the controller 33B has determined that it has not converged, the process proceeds to step S406B.

(S406B)

The controller 33B determines whether the iteration count n is the upper limit value L. When the iteration count n is the upper limit value L, the process proceeds to step S5B in FIG. 6. When the iteration count n is not the upper limit value L, the process proceeds to step S407B.

(S407B)

The controller 33B receives the image data generated by the reconstruction unit 32 in step S402B, and obtains a variance or standard deviation of pixels contained in the image as a variation value. At this time, the controller 33B calculates a variance or standard deviation of pixels contained in the image.

(S408B)

The controller 33B compares the variance or the standard deviation thus obtained to the second reference value stored in advance. When the variance or the standard deviation is not equal to or larger than the second reference value, the process proceeds to step S411B. When the variance or the standard deviation is equal to or larger than the second reference value, the process proceeds to step S409B.

(S409B)

The controller 33B issues an instruction to reduce the number of subsets and the reduced number of subsets to the reconstruction unit 32, and changes the maximum value M to a new subset count after the reduction. Further, the controller 33B retrieves the second reference value associated with the new subset count from the storage device.

(S410B)

The controller 33B controls the reconstruction unit 32 to divide the projection data into subsets as many as the new subset count.

(S411B)

The controller 33B controls the reconstruction unit 32 to increment the iteration count n. The controller 33B further controls the reconstruction unit 32 to change the subset number m to "1".

(S5B)

Under the control of the controller 33B, the display controller 330 receives the image data from the reconstruction unit 32. The display controller 330 generates an image representing the internal structure of the subject E, and displays the image on the display 34. Thus, the operation illustrated in FIG. 6 is completed.

According to this embodiment, the medical imaging apparatus 1 includes the detectors 11, the reconstruction unit 32, and the controller 33B. The detectors 11 are configured to detect radiation. The reconstruction unit 32 is configured to receive projection data that is based on the radiation detected by the detectors 11, divide the projection data into a plurality of subsets, and apply a reconstruction process to the subsets by successive approximation to successively generate images. The controller 33B is configured to monitor a course of the reconstruction process performed by the reconstruction unit 32, and control the reconstruction unit 32 to reduce a subset count indicating the number of subsets based on a variation value obtained by monitoring. Besides, the controller 33B is configured to obtain a variance or standard deviation of pixels included in the images as the variation value, and control the reconstruction unit 32 to reduce the subset count based on the variance or standard deviation. In this manner, the medical imaging apparatus 1 obtains a variance or standard deviation of pixels included in images as a variation value for the reconstruction process, and reduces the number of subsets based on the variation value. That is, the medical imaging apparatus 1 operates such that the subset count is larger in the early stage of the reconstruction process, while the subset count is reduced in the late stage. Thus, the medical imaging apparatus 1 can achieve less reconstruction process time as well as improved image quality.

Third Embodiment

Configuration

Figure 8:
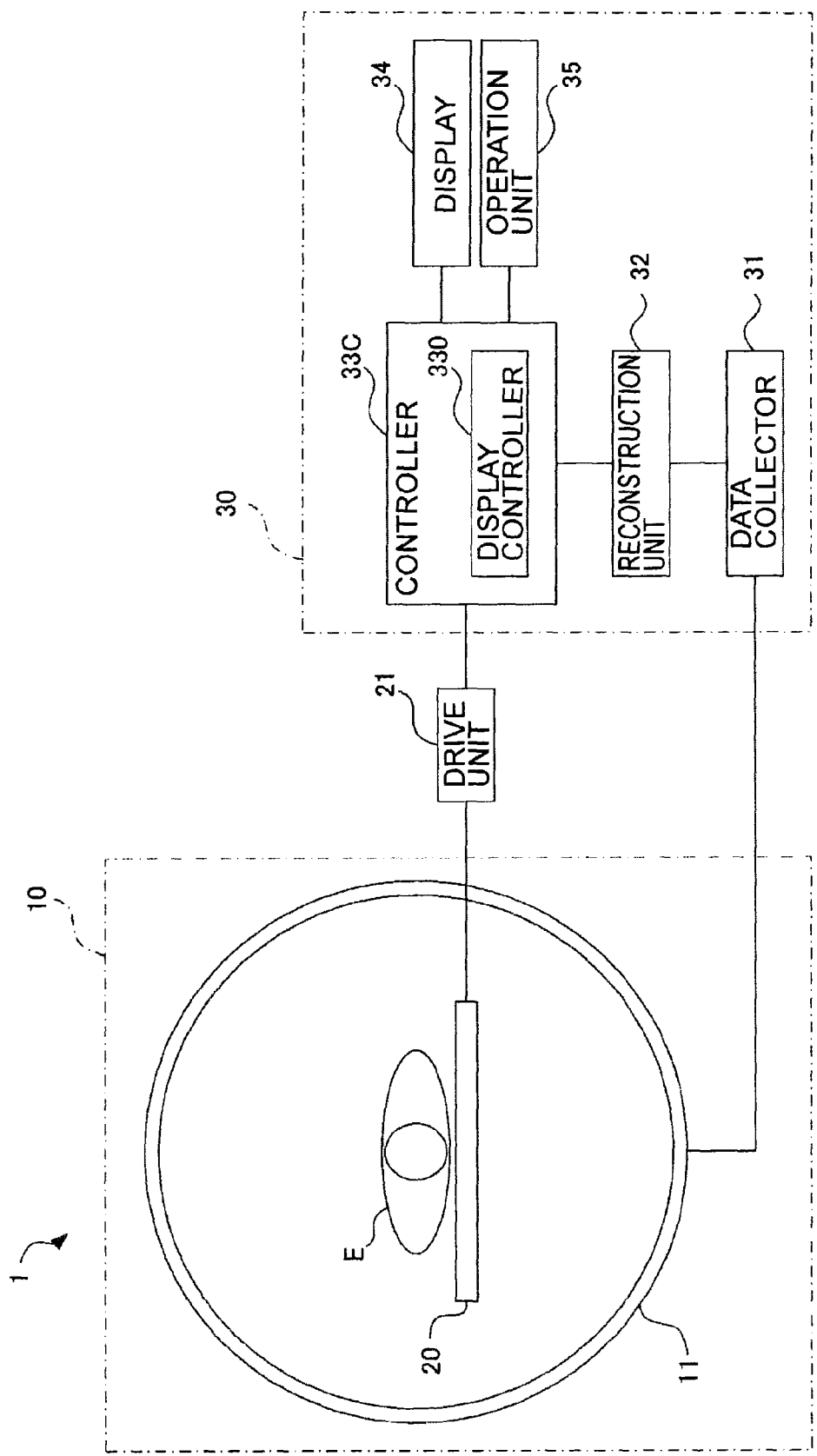
FIG. 8 is a block diagram illustrating the configuration of a medical imaging apparatus according to an embodiment.

FIG. 8 is a block diagram of the medical imaging apparatus 1 according to a third embodiment. The third embodiment is different from the first embodiment in the configuration of a controller 33C. Otherwise, this embodiment is similar to the first embodiment.

The controller 33C obtains the iteration count n indicating the number of iterations of the successive approximation performed by the reconstruction unit 32 as a variation value, and controls the reconstruction unit 32 to reduce the number of subsets based on the iteration count. Here, the iteration count represents the number of times a round of the approximation process for each subset (the calculation of an estimated value) is performed. For example, when the number of subsets is "10", the reconstruction unit 32 performs the approximation process for each of the subsets with a subset number from "1" to "10", and further performs the approximation process for each of them. The number of repetitions is the iteration count. The iteration count increases as the reconstruction process proceeds. Accordingly, the controller 33C monitors the iteration count as a variation value to determine the progress of the reconstruction process. For example, the controller 33C increments the iteration count each time the reconstruction unit 32 performs iterative approximation to obtain the iteration count.

The controller 33C includes, for example, a processing unit and a storage device. The storage device of the controller 33C stores in advance a third reference value for determining the progress of the reconstruction process. For example, the storage device stores, in stages, a plurality of iteration counts each as a variation value in association with the third reference value. The controller 33C compares the iteration count to the third reference value. When the iteration count is equal to or larger than the third reference value, the controller 33C issues an instruction to reduce the number of subsets to the reconstruction unit 32. Besides, when issuing the instruction to reduce the number of subsets to the reconstruction unit 32, the controller 33C also outputs the reduced number of subsets.

[Operation]

Figure 9:
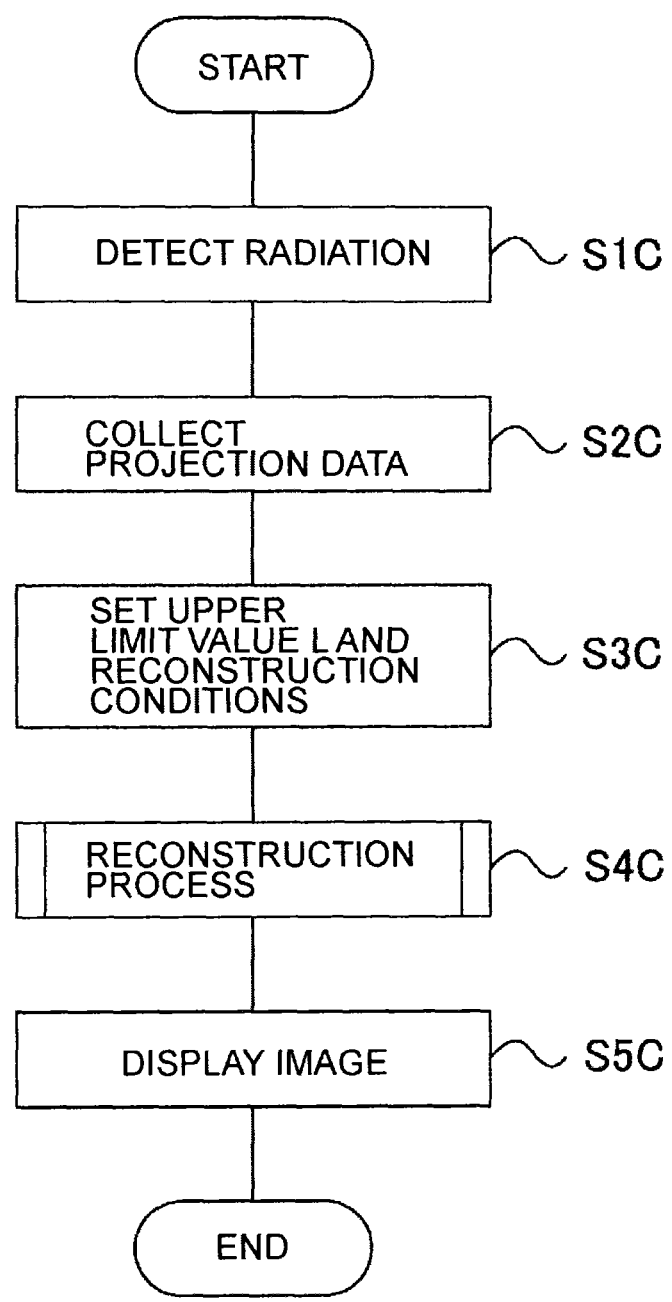
FIG. 9 is a flowchart of the operation of the medical imaging apparatus of the embodiment.
Figure 10:
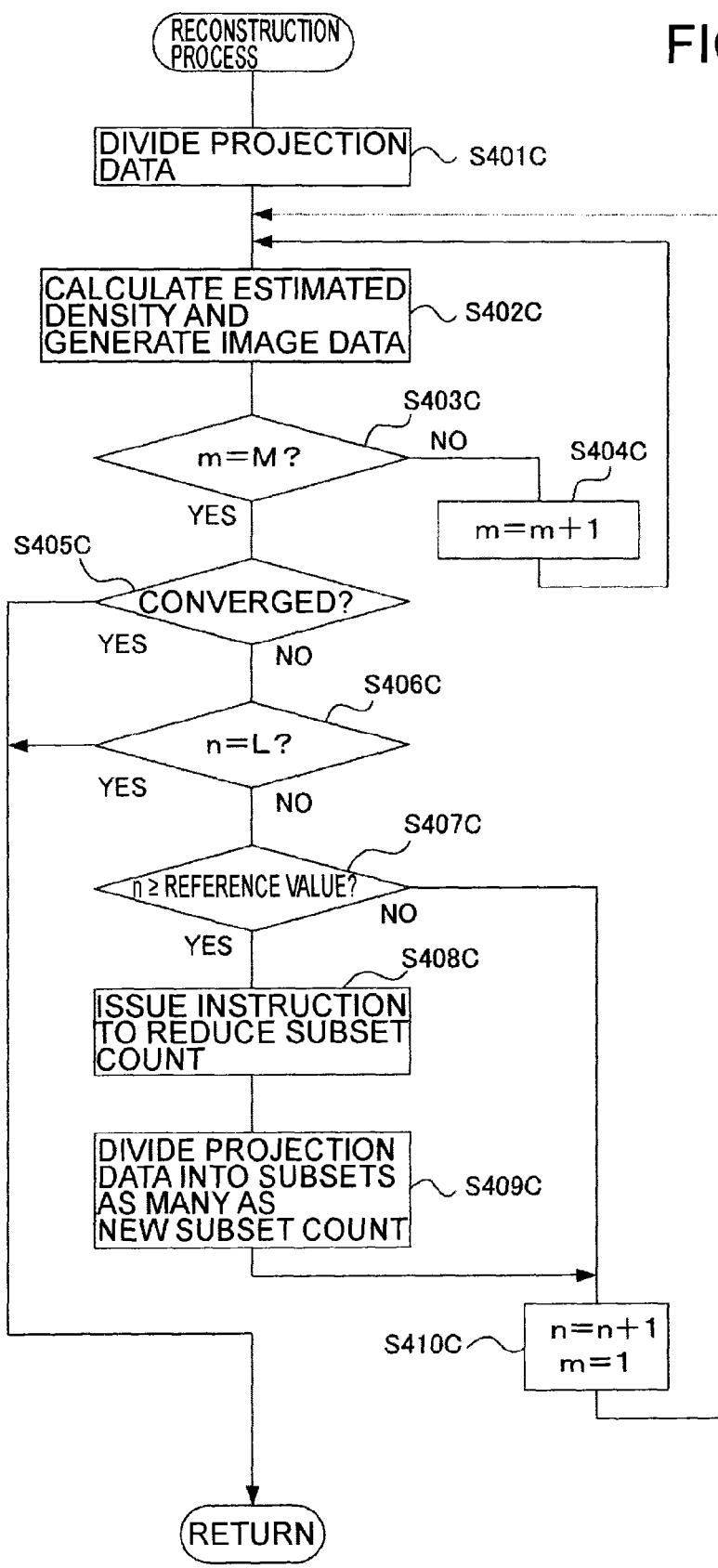
FIG. 10 is a flowchart of the operation of the medical imaging apparatus of the embodiment.

FIGS. 9 and 10 are flowcharts illustrating the operation of the medical imaging apparatus 1 of this embodiment.

(S1C)

The subject E is placed on the couch 20, and is inserted into the opening of the detectors 11. The controller 33C controls the detectors 11 to detect radiation from the subject E. The detectors 11 output the detection result to the data collector 31.

(S2C)

Under the control of the controller 33C, the data collector 31 receives the detection result of the detectors 11, and collects projection data by quantum counting the radiation according to the detection result. The data collector 31 outputs the projection data to the reconstruction unit 32.

(S3C)

The controller 33C sets a subset count and the upper limit value L of the iteration count n as reconstruction conditions. The reconstruction conditions may include various items (may be referred to as "condition items") as other conditions. Examples of the condition items include a field of view (FOV). The FOV is a condition item which defines the field size. The FOV is set with reference to an image based on the projection data. Alternatively, a predetermined FOV may be set automatically.

(S4C)

Under the control of the controller 33C, the reconstruction unit 32 receives the projection data generated based on the radiation detected by the detectors 11 from the data collector 31. The reconstruction unit 32 divides the projection data into a plurality of subsets based on the reconstruction conditions set in step S3C, and also applies the reconstruction process to the subsets by successive approximation to successively generate images. FIG. 10 is a flowchart illustrating the operation for the reconstruction process.

(S401C)

The reconstruction unit 32 divides the projection data received from the data collector 31 into a plurality of subsets. At this time, the number of the subsets is as many as the subset count set in step S3C.

(S402C)

The reconstruction unit 32 first performs the approximation process for the first subset (m=1) to calculate an estimated density of the position in the subject E corresponding to each voxel, and generates image data based on the estimated density calculated.

(S403C)

The reconstruction unit 32 determines whether the subset number m of the subset, for which the estimated density is calculated in step S402C, is the maximum value M. When the subset number m is not the maximum value M, the process proceeds to step S404C. When the subset number m is the maximum value M, it proceeds to step S405C.

(S404C)

The controller 33C controls the reconstruction unit 32 to increment the subset number m. Then, returning back to step S402C, the process is performed on a subset assigned with the subset number m incremented.

(S405C)

The controller 33C determines whether the estimated density calculated has converged. The controller 33C may make this determination by a general method such as using a log likelihood function. When the controller 33C has determined that the estimated density has converged, the process proceeds to step S5C in FIG. 9. When the controller 33C has determined that it has not converged, the process proceeds to step S406C.

(S406C)

The controller 33C determines whether the iteration count n is the upper limit value L. When the iteration count n is the upper limit value L, the process proceeds to step S5C in FIG. 9. When the iteration count n is not the upper limit value L, the process proceeds to step S407C.

(S407C)

The controller 33C compares the iteration count n to the third reference value stored in advance. When the iteration count n is not equal to or larger than the third reference value, the process proceeds to step S410C. When the iteration count n is equal to or larger than the third reference value, the process proceeds to step S408C.

(S408C)

The controller 33C issues an instruction to reduce the number of subsets and the reduced number of subsets to the reconstruction unit 32, and changes the maximum value M to a new subset count after the reduction. Further, the controller 33C retrieves the third reference value associated with the new subset count from the storage device.

(S409C)

The controller 33C controls the reconstruction unit 32 to divide the projection data into subsets as many as the new subset count.

(S410C)

The controller 33C controls the reconstruction unit 32 to increment the iteration count n. The controller 33C further controls the reconstruction unit 32 to change the subset number m to "1".

(S5C)

Under the control of the controller 33C, the display controller 330 receives the image data from the reconstruction unit 32. The display controller 330 generates an image representing the internal structure of the subject E, and displays the image on the display 34. Thus, the operation illustrated in FIG. 9 is completed.

According to this embodiment, the medical imaging apparatus 1 includes the detectors 11, the reconstruction unit 32, and the controller 33C. The detectors 11 are configured to detect radiation. The reconstruction unit 32 is configured to receive projection data that is based on the radiation detected by the detectors 11, divide the projection data into a plurality of subsets, and apply a reconstruction process to the subsets by successive approximation to successively generate images. The controller 33C is configured to monitor a course of the reconstruction process performed by the reconstruction unit 32, and control the reconstruction unit 32 to reduce a subset count indicating the number of subsets based on a variation value obtained by monitoring. Besides, the controller 33C is configured to obtain an iteration count indicating the number of iterations of the successive approximation performed by the reconstruction unit 32 as the variation value, and control the reconstruction unit 32 to reduce the number of subsets based on the iteration count. In this manner, the medical imaging apparatus 1 obtains an iteration count indicating the number of iterations of the successive approximation performed by the reconstruction unit 32 as a variation value for the reconstruction process, and reduces the number of subsets based on the variation value. That is, the medical imaging apparatus 1 operates such that the subset count is larger in the early stage of the reconstruction process, while the subset count is reduced in the late stage. Thus, the medical imaging apparatus 1 can achieve less reconstruction process time as well as improved image quality.

Fourth Embodiment

Configuration

Figure 11:
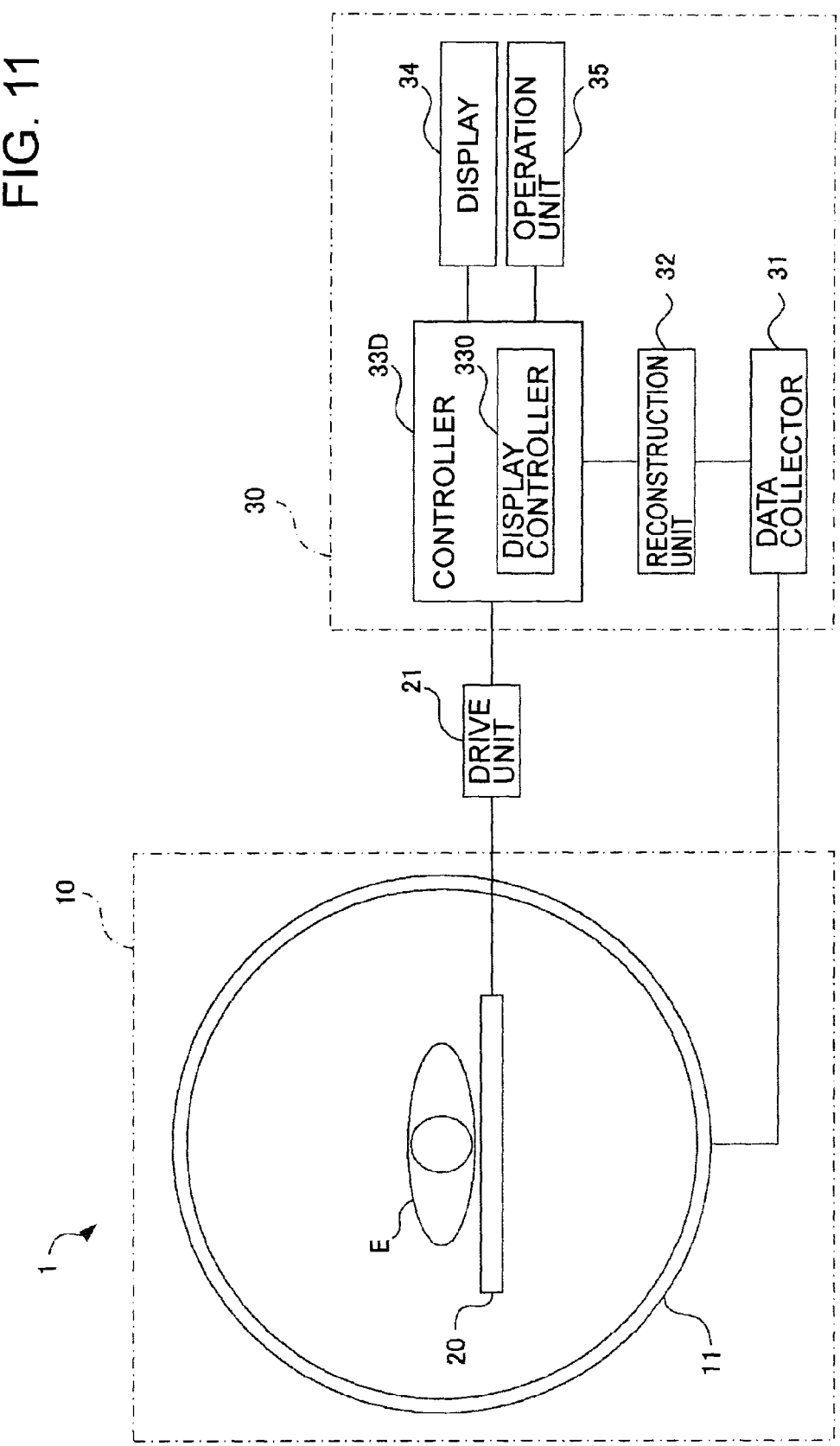
FIG. 11 is a block diagram illustrating the configuration of a medical imaging apparatus according to an embodiment.

FIG. 11 is a block diagram of the medical imaging apparatus 1 according to a fourth embodiment. The fourth embodiment is different from the first embodiment in the configuration of a controller 33D. Otherwise, this embodiment is similar to the first embodiment.

The controller 33D obtains an update count indicating the number of times the reconstruction unit 32 performs successive approximation for image update as a variation value, and controls the reconstruction unit 32 to reduce the number of subsets based on the update count. Here, the update count represents the number of times the reconstruction unit 32 performs an approximation process (the calculation of an estimated value) with respect to subsets. For example, when the number of subsets is "10", if the approximation process is performed on each of the 10 subsets, the update count is "10". The update count increases as the reconstruction process proceeds. Accordingly, the controller 33D monitors the update count as a variation value to determine the progress of the reconstruction process. For example, the controller 33D increments the update count each time the reconstruction unit 32 performs the approximation process (the calculation of an estimated value) with respect to a subset to obtain the update count.

The controller 33D includes, for example, a processing unit and a storage device. The storage device of the controller 33D stores in advance a fourth reference value for determining the progress of the reconstruction process. For example, the storage device stores, in stages, a plurality of update counts each as a variation value in association with the fourth reference value. The controller 33D compares the update count to the fourth reference value. When the update count is equal to or larger than the fourth reference value, the controller 33D issues an instruction to reduce the number of subsets to the reconstruction unit 32. Besides, when issuing the instruction to reduce the number of subsets to the reconstruction unit 32, the controller 33D also outputs the reduced number of subsets.

[Operation]

Figure 12:
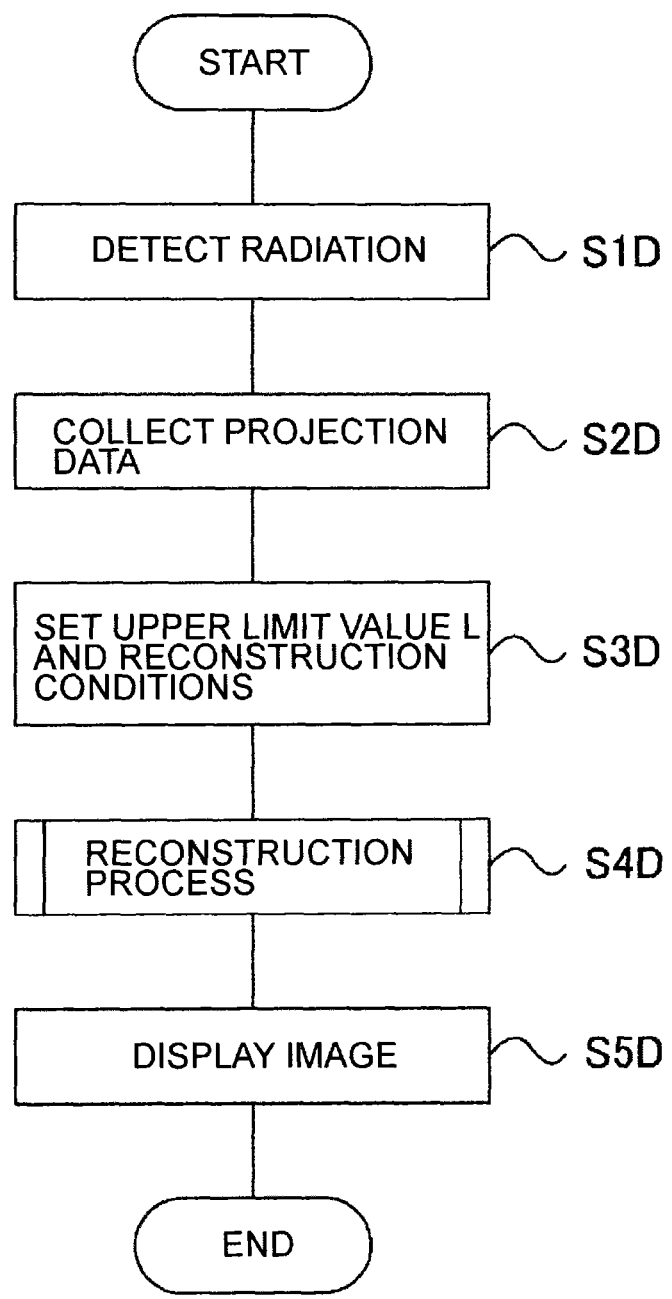
FIG. 12 is a flowchart of the operation of the medical imaging apparatus of the embodiment.
Figure 13:
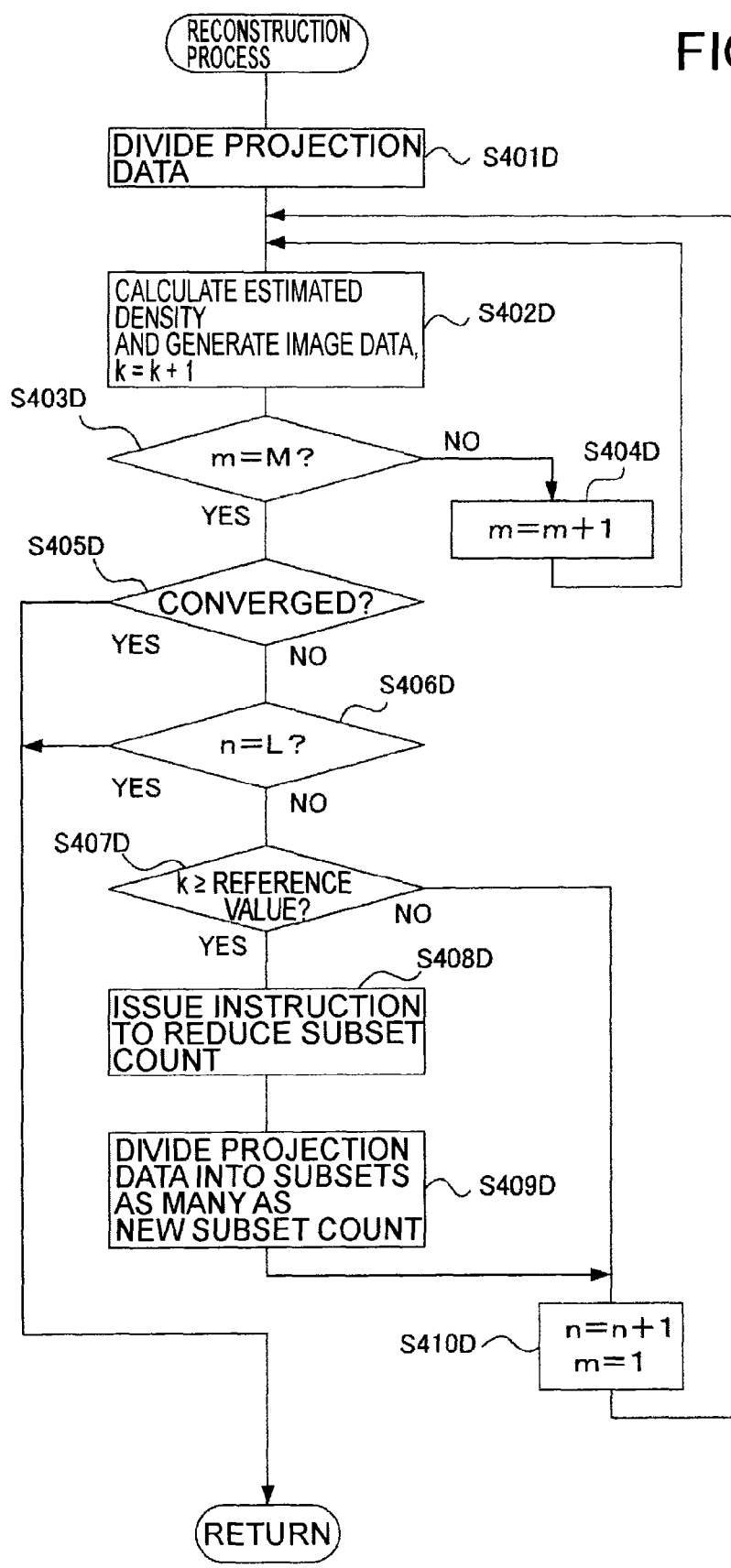
FIG. 13 is a flowchart of the operation of the medical imaging apparatus of the embodiment.

FIGS. 12 and 13 are flowcharts illustrating the operation of the medical imaging apparatus 1 of this embodiment.

(S1D)

The subject E is placed on the couch 20, and is inserted into the opening of the detectors 11. The controller 33D controls the detectors 11 to detect radiation from the subject E. The detectors 11 output the detection result to the data collector 31.

(S2D)

Under the control of the controller 33D, the data collector 31 receives the detection result of the detectors 11, and collects projection data by quantum counting the radiation according to the detection result. The data collector 31 outputs the projection data to the reconstruction unit 32.

(S3D)

The controller 33D sets a subset count and the upper limit value L of the iteration count n as reconstruction conditions. The reconstruction conditions may include various items (may be referred to as "condition items") as other conditions. Examples of the condition items include a field of view (FOV). The FOV is a condition item which defines the field size. The FOV is set with reference to an image based on the projection data. Alternatively, a predetermined FOV may be set automatically.

(S4D)

Under the control of the controller 33D, the reconstruction unit 32 receives the projection data generated based on the radiation detected by the detectors 11 from the data collector 31. The reconstruction unit 32 divides the projection data into a plurality of subsets based on the reconstruction conditions set in step S3D, and also applies the reconstruction process to the subsets by successive approximation to successively generate images. FIG. 13 is a flowchart illustrating the operation for the reconstruction process.

(S401D)

The reconstruction unit 32 divides the projection data received from the data collector 31 into a plurality of subsets. At this time, the number of the subsets is as many as the subset count set in step S3D.

(S402D)

The reconstruction unit 32 first performs the approximation process for the first subset (m=1) to calculate an estimated density of the position in the subject E corresponding to each voxel, and generates image data based on the estimated density calculated. Then, the reconstruction unit 32 increments the update count k.

(S403D)

The reconstruction unit 32 determines whether the subset number m of the subset, for which the estimated density is calculated in step S402D, is the maximum value M. When the subset number m is not the maximum value M, the process proceeds to step S404D. When the subset number m is the maximum value M, it proceeds to step S405D.
(S404D)
The controller 33D controls the reconstruction unit 32 to increment the subset number m. Then, returning back to step S402D, the process is performed on a subset assigned with the subset number m incremented.
(S405D)
The controller 33D determines whether the estimated density calculated has converged. The controller 33D may make this determination by a general method such as using a log likelihood function. When the controller 33D has determined that the estimated density has converged, the process proceeds to step S5D in FIG. 12. When the controller 33D has determined that it has not converged, the process proceeds to step S406D.
(S406D)
The controller 33D determines whether the iteration count n is the upper limit value L. When the iteration count n is the upper limit value L, the process proceeds to step S5D in FIG. 12. When the iteration count n is not the upper limit value L, the process proceeds to step S407D.
(S407D)
The controller 33D compares the update count k to the fourth reference value stored in advance. When the update count k is not equal to or larger than the fourth reference value, the process proceeds to step S410D. When the update count k is equal to or larger than the fourth reference value, the process proceeds to step S408D.
(S408D)
The controller 33D issues an instruction to reduce the number of subsets and the reduced number of subsets to the reconstruction unit 32, and changes the maximum value M to a new subset count after the reduction. Further, the controller 33D retrieves the fourth reference value associated with the new subset count from the storage device.
(S409D)
The controller 33D controls the reconstruction unit 32 to divide the projection data into subsets as many as the new subset count.
(S410D)
The controller 33D controls the reconstruction unit 32 to increment the iteration count n. The controller 33D further controls the reconstruction unit 32 to change the subset number m to "1".
(S5D)
Under the control of the controller 33D, the display controller 330 receives the image data from the reconstruction unit 32. The display controller 330 generates an image representing the internal structure of the subject E, and displays the image on the display 34. Thus, the operation illustrated in FIG. 12 is completed.

According to this embodiment, the medical imaging apparatus 1 includes the detectors 11, the reconstruction unit 32, and the controller 33D. The detectors 11 are configured to detect radiation. The reconstruction unit 32 is configured to receive projection data that is based on the radiation detected by the detectors 11, divide the projection data into a plurality of subsets, and apply a reconstruction process to the subsets by successive approximation to successively generate images. The controller 33D is configured to monitor a course of the reconstruction process performed by the reconstruction unit 32, and control the reconstruction unit 32 to reduce a subset count indicating the number of subsets based on a variation value obtained by monitoring. Besides, the controller 33D is configured to obtain an update count indicating the number of times the reconstruction unit 32 performs successive approximation for image update as a variation value, and control the reconstruction unit 32 to reduce the number of subsets based on the update count. In this manner, the medical imaging apparatus 1 obtains an update count indicating the number of times the reconstruction unit 32 performs successive approximation as a variation value for the reconstruction process, and reduces the number of subsets based on the variation value. That is, the medical imaging apparatus 1 operates such that the subset count is larger in the early stage of the reconstruction process, while the subset count is reduced in the late stage. Thus, the medical imaging apparatus 1 can achieve less reconstruction process time as well as improved image quality.

First Modification

Configuration

Figure 14:
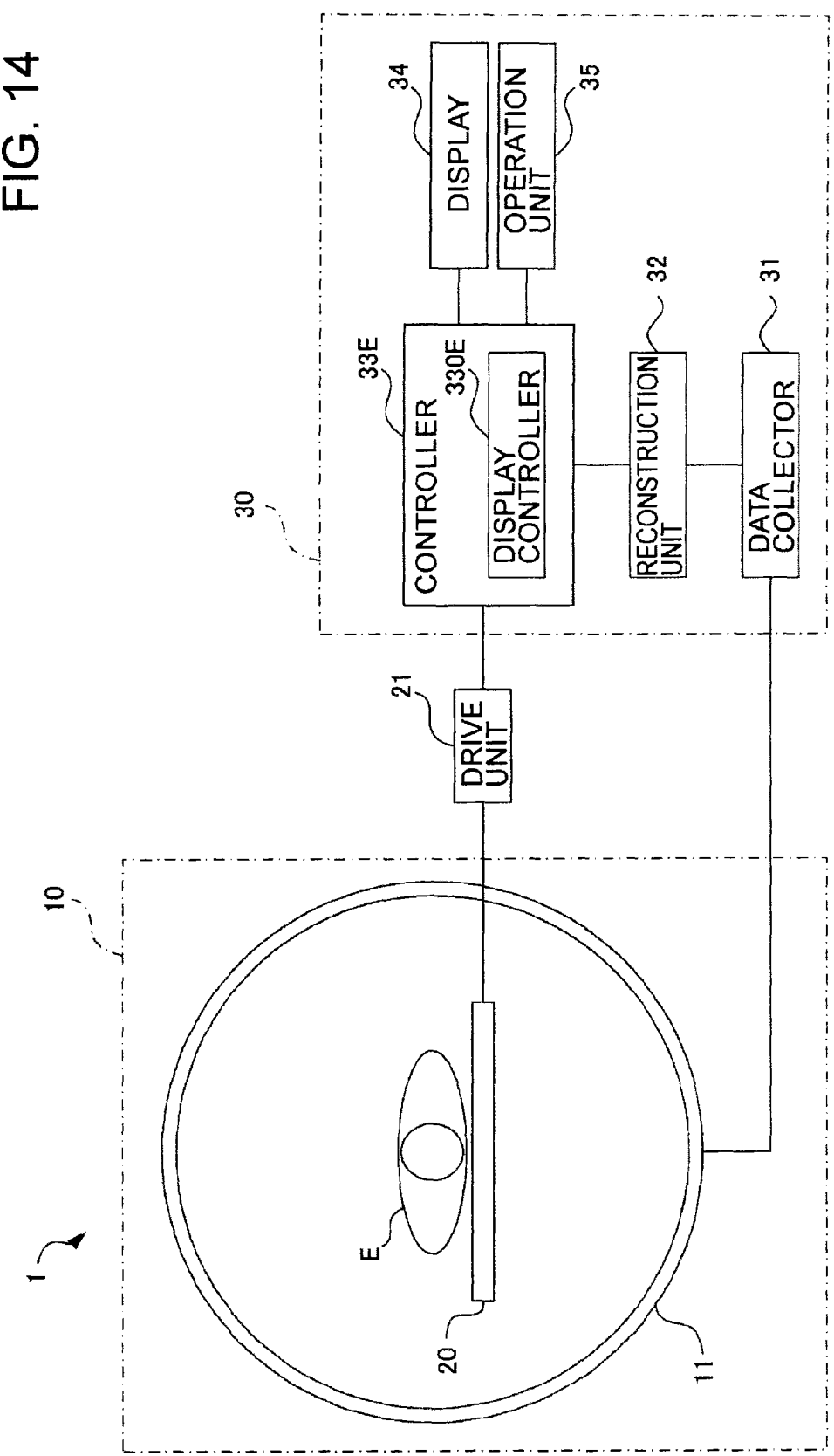
FIG. 14 is a block diagram illustrating the configuration of a medical imaging apparatus according to an embodiment.

FIG. 14 is a block diagram of the medical imaging apparatus 1 according to a first modification. The first modification is different from the first to fourth embodiments in the configuration of a controller 33E and a display controller 330E. Otherwise, this modification is similar to the first embodiment.

The controller 33E includes the display controller 330E. The display controller 330E sequentially displays images and/or variation values on the display 34. Upon receipt of a reduction instruction from the operation unit 35, the display controller 330E controls the reconstruction unit 32 to reduce the number of subsets based on the reduction instruction. The display controller 330E receives image data being subjected to the reconstruction process from the reconstruction unit 32, and applies the same process as performed in the first embodiment to the image data to display it as an image. The controller 33E successively receives variation values from the reconstruction unit 32, and sequentially outputs them to the display controller 330E. The display controller 330E sequentially displays the variation values received from the controller 33E on the display 34. The controller 33E successively obtains, as a variation value, at least one of a difference or a ratio of average values of pixel values contained in ROIs, a variance or standard deviation of pixel values of images, an iteration count indicating the number of iterations of the successive approximation performed by the reconstruction unit 32, and an update count indicating the number of times the reconstruction unit 32 performs successive approximation for image update, and outputs it to the display controller 330E. That is, the display controller 330E of the first modification is configured to sequentially display pieces of information used as variation values in the first to fourth embodiments on the display 34.

Figure 15:
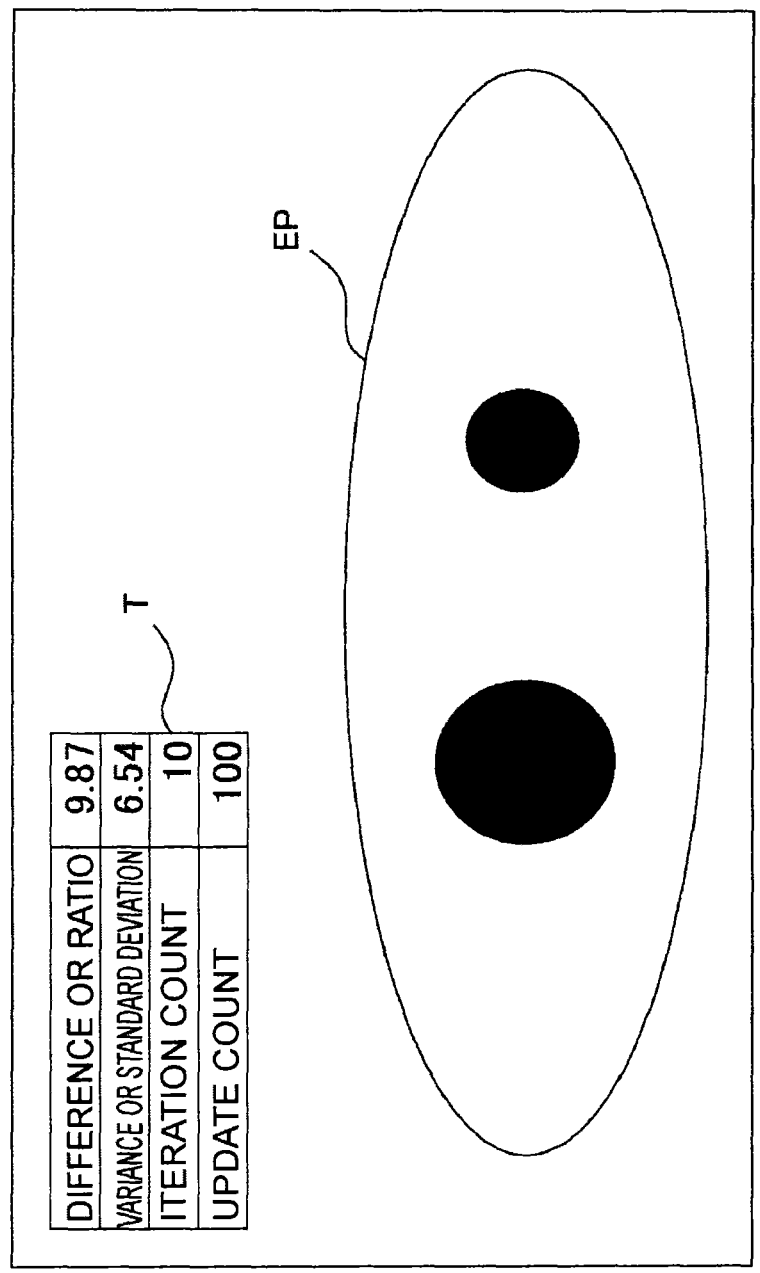
FIG. 15 is a schematic diagram illustrating the outline of the medical imaging apparatus of the embodiment.

FIG. 15 is a schematic diagram illustrating an example of an image and variation values that the display controller 330E displays on the display 34. For example, the display controller 330E displays on the display 34 an image EP, which is being reconstructed, together with variation values T in a table format. The operator checks the progress of the reconstruction process based on the display of the variation values, and enters an instruction to reduce the number of subsets via the operation unit 35. The controller 33E receives the reduction instruction from the operation unit 35, and controls the reconstruction unit 32 to reduce the number of subsets based on the instruction. Note that a new subset count after the reduction may be set in advance, or may be set by the operator through the operation unit 35 when he/she enters the reduction instruction.

According to this modification, the medical imaging apparatus 1 includes the detectors 11, the reconstruction unit 32, and the controller 33E. The detectors 11 are configured to detect radiation. The reconstruction unit 32 is configured to receive projection data that is based on the radiation detected by the detectors 11, divide the projection data into a plurality of subsets, and apply a reconstruction process to the subsets by successive approximation to successively generate images. The controller 33E is configured to monitor a course of the reconstruction process performed by the reconstruction unit 32, and control the reconstruction unit 32 to reduce a subset count indicating the number of subsets based on a variation value obtained by monitoring. The controller 33E includes the display controller 330E configured to sequentially display on the display 34 an image and/or the variation value. Upon receipt of a reduction instruction from the operation unit 35, the controller 33E controls the reconstruction unit 32 to reduce the number of subsets based on the reduction instruction. Thus, the medical imaging apparatus 1 can achieve less reconstruction process time as well as improved image quality.

Fifth Embodiment

Configuration

Figure 16:
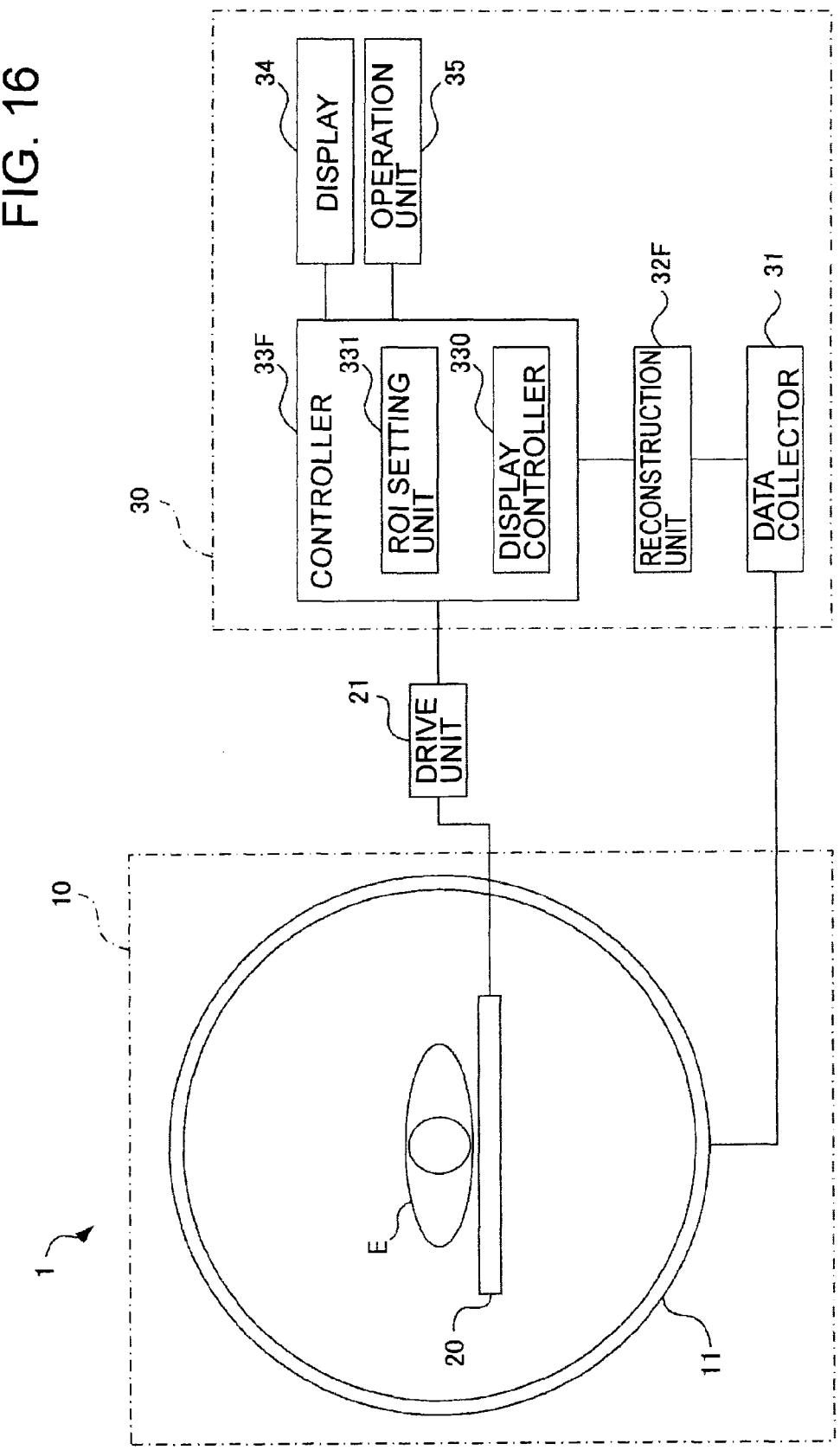
FIG. 16 is a block diagram illustrating the configuration of a medical imaging apparatus according to an embodiment.

FIG. 16 is a block diagram of the medical imaging apparatus 1 according to a fifth embodiment. The fifth embodiment is different from the first embodiment in the configuration of a reconstruction unit 32F. Otherwise, this embodiment is similar to the first embodiment.

The reconstruction unit 32F performs weighting of projection data based on a ROI. For example, with reference to the coordinates of the ROI and those of the projection data, the reconstruction unit 32F assigns a heavier weight to projection data with coordinates closer to the center of the ROI, and a lighter weight to projection data with coordinates farther from the center of the ROI. The setting of a coordinate system that defines the coordinates of the ROI and those of the projection data and the reference thereto can be performed using a common technology.

The reconstruction unit 32F divides the projection data into a plurality of subsets based on the weighting. For example, with reference to the weighting of projection data and the subset count, the reconstruction unit 32F divides projection data into a plurality of subsets such that pieces of projection data each having a similar weight are in the same subset. This corresponds to the generation of subset ranging from one including many pieces of projection data with coordinates closer to the center of the ROI to one including many pieces of projection data with coordinates far from the center of the ROI.

The reconstruction unit 32F applies the reconstruction process to a heavily weighted subset after a lightly weighted subset. The heavily weighted subset is a subset including many pieces of projection data having a heavy weight. The lightly weighted subset is a subset including many pieces of projection data having a light weight. For example, the reconstruction unit 32F obtains, for each subset, a value indicating the weight of the subset such as the average or total of the weights of projection data included in the subset. The heavier weight the value indicates, the later the reconstruction unit 32F applies the reconstruction process to the subset. For example, the reconstruction unit 32F assigns a large subset number m to a heavier subset, and a small subset number m to a lighter subset. With this, the reconstruction unit 32F can apply the reconstruction process to the heavier subset after the lighter subset.

[Operation]

The operation of the reconstruction unit 32F can replace step S401A in FIG. 4, step S401B in FIG. 7, step S401C in FIG. 10, and step S401D of FIG. 13.

According to this embodiment, the medical imaging apparatus 1 includes the reconstruction unit 32F. The reconstruction unit 32F performs weighting of projection data based on a ROI. The reconstruction unit 32F divides the projection data into a plurality of subsets based on the weighting. The reconstruction unit 32F applies the reconstruction process to a heavier subset after a lighter subset. In this manner, the medical imaging apparatus 1 of this embodiment generates a subset including many pieces of projection data assigned with a heavier weight with respect to the coordinates of a ROI. In addition, the medical imaging apparatus 1 applies the successive approximation reconstruction process to a heaver subset later in the order. This corresponds to applying the successive approximation reconstruction process to projection data in the coordinates of the ROI later in the order. If the successive approximation reconstruction process is applied later, estimated values obtained by the previous process can be reflected. Thus, the medical imaging apparatus can obtain a highly accurate estimated value with respect to the ROI.

Second Modification

Figure 17:
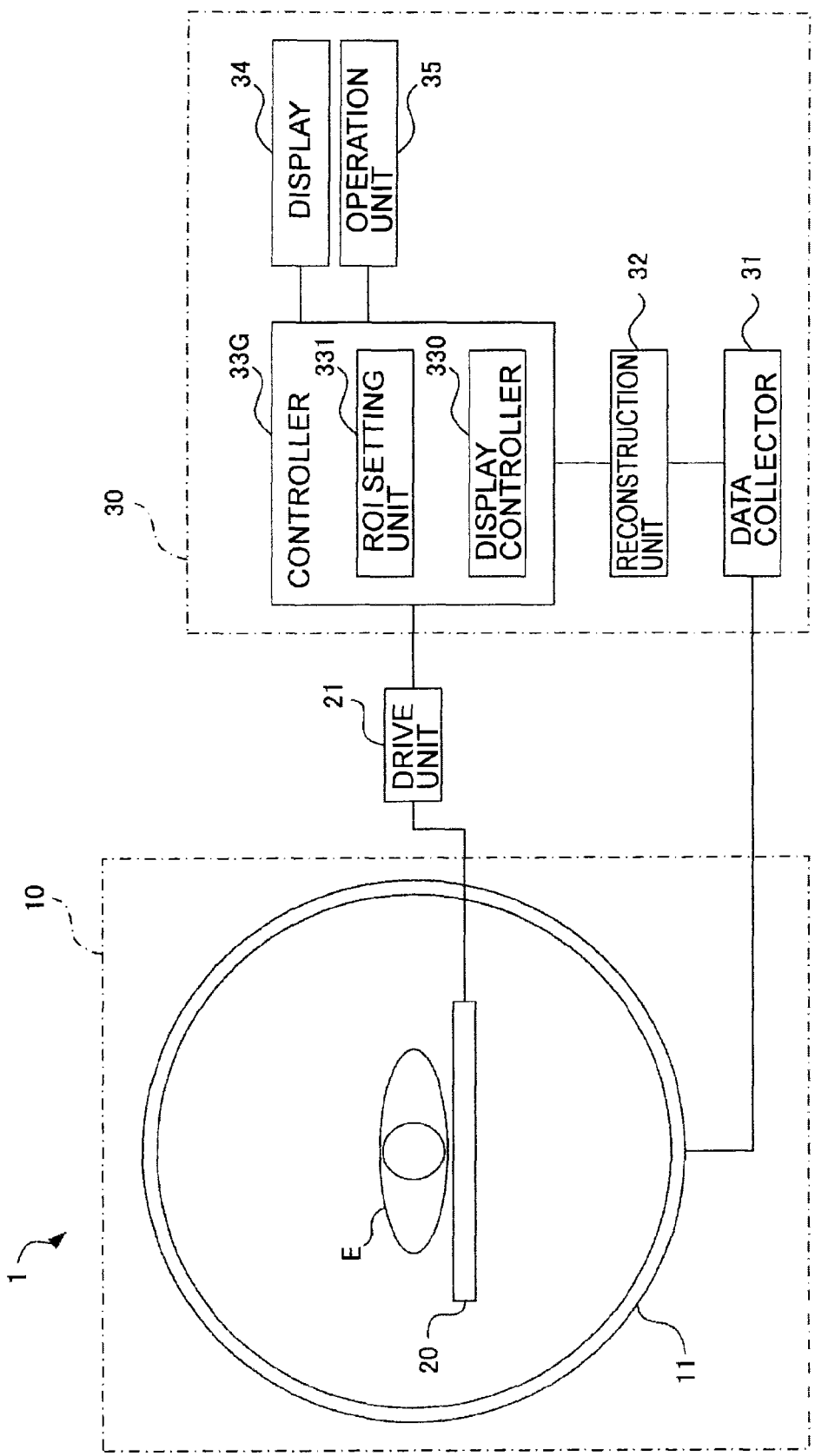
FIG. 17 is a block diagram illustrating the configuration of a medical imaging apparatus according to an embodiment.

FIG. 17 is a block diagram of the medical imaging apparatus 1 according to a second modification. The second modification is different from the first to fifth embodiments in the configuration of a controller 33G. For other components, the configuration of the first embodiment can be adopted as appropriate.

Having received an instruction to change a ROI from the operation unit 35, the controller 33G calculates a variation value based on a ROI after the change. For example, a ROI initially set may be off from a site where clinical observation is desired. In this case, the user may enter an instruction to the controller 33G to change the ROI to the coordinates of the site where clinical observation is desired through the operation unit during the reconstruction process. Based on the coordinates of the ROI after being changed, the controller 33G obtains a variation value with respect to the coordinates in an image being reconstructed. In this manner, when receiving an instruction to change the ROI via the operation unit during the reconstruction process, the controller 33G can obtain a variation value representing a change in image quality with respect to a site where clinical observation is desired for the rest of the reconstruction process. If a ROI initially set is off from a site where clinical observation is desired, upon receipt of an instruction to change the ROI, the medical imaging apparatus changes the number of subsets depending on the image quality regarding the site where clinical observation is desired. Thus, the medical imaging apparatus can achieve less reconstruction process time as well as improved image quality. Incidentally, the controller 33G may receive the instruction to change the ROI at any time in the process of steps S401A to S411 in FIG. 4 or steps S401B to S411B in FIG. 7. Through step S407A or S407B performed after the receipt of the instruction, the controller 33G obtains a variation value with respect to the ROI after the change.

While certain embodiments have been described, these embodiments have been presented by way of example only, and are not intended to limit the scope of the inventions.

Indeed, the novel embodiments described herein may be embodied in a variety of other forms; further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical imaging apparatus, comprising
a detector configured to detect radiation; and
processing circuitry configured to
receive projection data that is based on the radiation detected by the detector, divide the projection data into a plurality of subsets, and apply a reconstruction process to the subsets by successive approximation to successively generate images,
set a region of interest in the images, and
obtain a variation value indicating a change in image quality from the images, and, when the variation value reaches a predetermined value, set a new subset count less than the number of the subsets, and sequentially reconstruct subsets as many as the new subset count into an image,
wherein the processing circuitry is further configured to assign a weight to the projection data based on the region of interest, and divide the projection data into the subsets based on the weight.

2. The medical imaging apparatus of claim 1, wherein the processing circuitry is further configured to apply the reconstruction process to a subset assigned with a heavier weight after a subset assigned with a lighter weight.

3. The medical imaging apparatus of claim 1, wherein the processing circuitry is further configured to obtain an iteration count indicating the number of iterations of the successive approximation as the variation value, and reduce the number of the subsets based on the iteration count.

4. The medical imaging apparatus of claim 1, wherein the processing circuitry is further configured to obtain an update count indicating the number of times an image is updated by the successive approximation as the variation value, and reduce the number of the subsets based on the update count.

5. The medical imaging apparatus of claim 1, wherein the processing circuitry is further configured to obtain a, difference or a ratio of average values of pixel values contained in regions of interest as the variation value, and reduce the number of the subsets based on the difference or the ratio.

6. The medical imaging apparatus of claim 1, wherein the processing circuitry is further configured to obtain a variance or standard deviation of pixel values of the images as the variation value, and reduce the number of the subsets based on the variance or the standard deviation.

7. The medical imaging apparatus of claim 1, further comprising an input circuit, wherein, having received an instruction to change the region of interest from the input circuit, the processing circuitry obtains the variation value based on a new region of interest.

8. The medical imaging apparatus of claim 1, further comprising an input circuit,
wherein the processing circuitry is further configured to sequentially display the images and/or the variation value on a display, and, having received a reduction instruction from the input circuit, reduce the number of the subsets based on the reduction instruction.

* * * * *